United States Patent [19]

DeFriez

[11] Patent Number: 5,187,972
[45] Date of Patent: Feb. 23, 1993

[54] GAS MONITOR

[75] Inventor: Herbert H. DeFriez, Carpinteria, Calif.

[73] Assignee: Clean Air Engineering, Inc., Palatine, Ill.

[21] Appl. No.: 822,294

[22] Filed: Jan. 17, 1992

[51] Int. Cl.⁵ ............................................. G01N 30/00
[52] U.S. Cl. ...................... 73/23.2; 73/29.02; 73/29.01
[58] Field of Search ............... 73/23.2, 29.01, 29.05, 73/31.05, 29.02

[56] References Cited

U.S. PATENT DOCUMENTS

| | | | |
|---|---|---|---|
| 1,100,171 | 6/1914 | Brown | 73/28.01 |
| 3,051,643 | 8/1962 | Bergson | 204/409 |
| 4,102,647 | 7/1978 | Roelse et al. | 436/40 |
| 4,361,027 | 11/1982 | Schmitt | 73/23.2 |
| 4,507,875 | 4/1985 | Hirsch et al. | 34/44 |
| 4,724,700 | 2/1988 | Jaasma | 73/29.01 |
| 4,739,647 | 4/1988 | Monticelli, Jr. | 73/23.2 |

FOREIGN PATENT DOCUMENTS 1-253631 10/1989 Japan .

Primary Examiner—Hezron E. Williams
Assistant Examiner—Michael Brock
Attorney, Agent, or Firm—Olson & Hierl, Ltd.

[57] ABSTRACT

A gas (including water vapor) monitor is provided which incorporates a dual chambered, constant volume peristaltic pump and flow meters. A sample gas is pumped at a constant volumetric flow rate into a processing zone where a predetermined component of the sample gas is separated. A make-up gas is then allowed to admix with the resulting gas and the mixture is then pumped at the same constant rate. The measured volume of the make-up gas thus required is equal to the actual volume of the separated component.

41 Claims, 12 Drawing Sheets

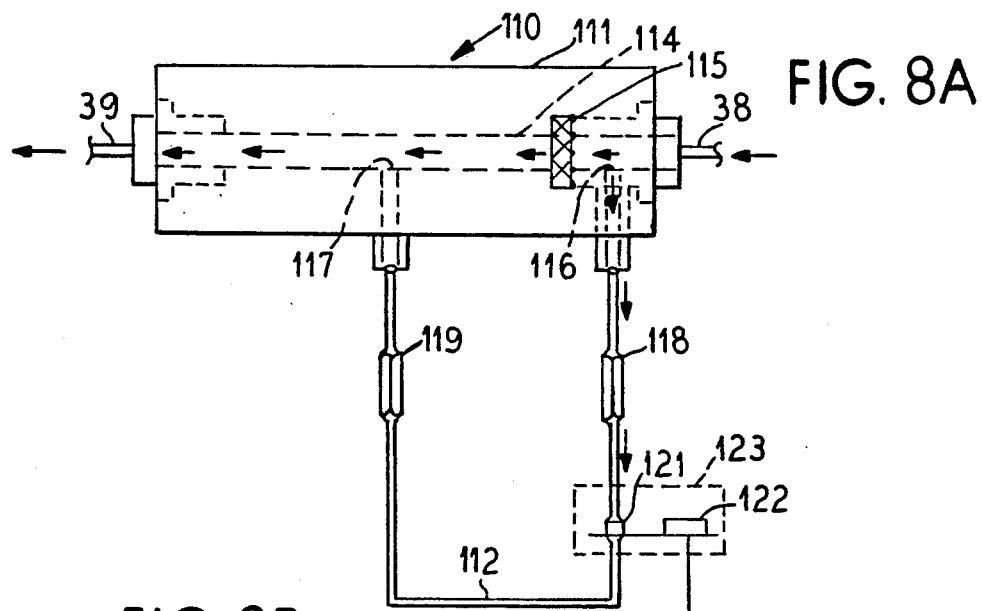
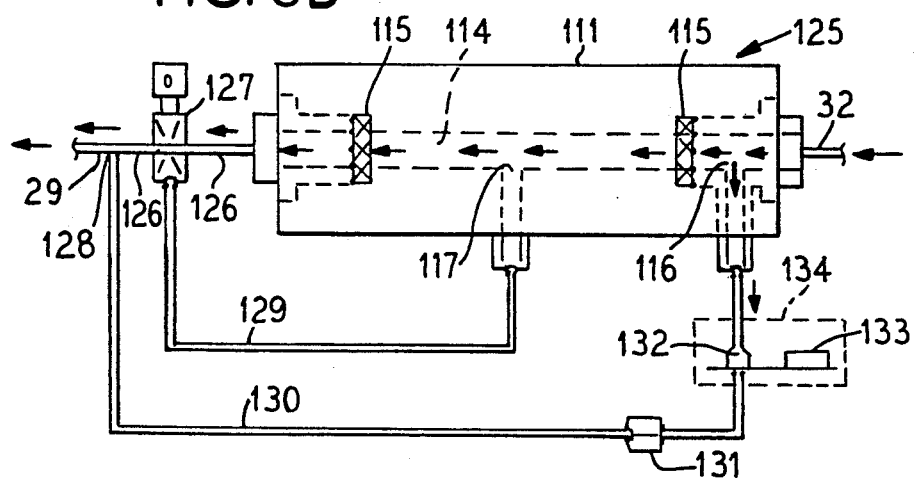
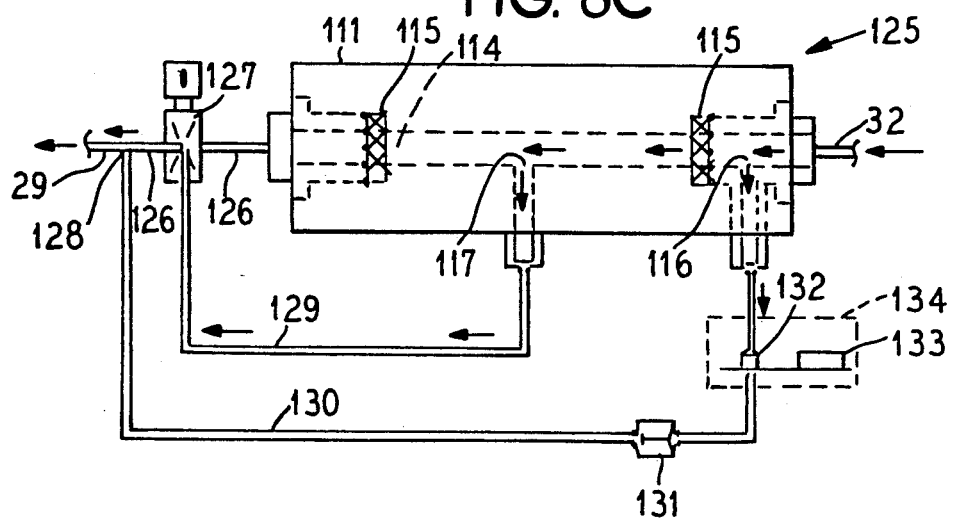

GAS MONITOR

FIELD OF THE INVENTION

This invention relates to a continuous gas and moisture monitor which includes a dual chambered constant volume peristaltic pump, gas separation means, gas mixing means and flow meter means.

BACKGROUND OF THE INVENTION

Devices for monitoring or analyzing gas (including moisture) have previously been proposed which use various measuring systems.

For example, the measuring systems employed in U.S. Pat. No. 4,724,700 to Jaasma and U.S. Pat. No. 4,507,875 to Hirsch et al. utilize a measured difference in gas flow rates before and after separation of a gaseous component, such as moisture. In Jaasma, the first flow rate measurement is made on partially dried gas; and in Hirsch et al., the first flow rate measurement is made on the entire starting gas.

In addition, U.S. Pat. No. 1,100,171 to Brown measures weight gain of a "moisture removing medium", Bergson (U.S. Pat. No. 3,051,643) utilizes an electrolysis cell and Roelse et al. (U.S. Pat. No. 4,102,647) uses an oleophilic substance which retains liquid hydrocarbon compounds. Moreover, infrared spectroscopy is being used in commercially available continuous moisture monitors to determine the moisture content of a sample.

Such prior art techniques and apparatus usually require trained personnel for operation, maintenance and repairs. Some of these systems are complex, and many are expensive to purchase, use and maintain, such as spectroscopic devices with their associated complex electrooptical assemblies. Others are not well-suited for continuous use or for use with automated and computerized controls, such as the systems which involve periodic measurement or monitoring, as described in the foregoing Brown and Roelse et al. patents.

A new and improved gas monitoring system is needed which uses simple, reliable mechanical hardware, requires little maintenance and repairs, and permits automated, computerized continuous operation. The present invention is directed to this need.

SUMMARY OF THE INVENTION

A gas and moisture monitor is provided which operates by separating a component of a sample gas, and then measuring the volume of the separated component by admixing a metered amount of a make-up gas with the resulting sample gas.

In the monitor, a sample gas is pumped at a constant volumetric flow rate into a selective gas separation zone. In this zone, at least one gaseous component is separated from the sample gas. In a presently preferred operating mode, the component separated in this zone is moisture and the separation means comprises a dryer. A make-up gas is then allowed to admix with the resulting gas to replace the volume of the separated component, and the resulting mixture is then pumped at the same volumetric flow rate. The measured volume of the make-up gas so admixed is equal to the actual volume of the separated component.

The inventive monitor incorporates constant volume pumping means both before the gas separation zone and after the make-up gas mixing. The pumping means is preferably provided by a dual chambered, constant volume peristaltic pump. The monitor also incorporates metering means for measuring the amount of make-up gas so admixed.

The monitor overcomes the disadvantages of the prior art devices for monitoring gas and is accurate, reliable, continuously operatable, relatively simple, efficient, and economical both structurally and operationally. Also, the monitor is well-suited for computer controlled, automatic functioning.

In a presently preferred embodiment, the monitor is adapted for moisture analysis, and in such form comprises a combination of a dual chambered peristaltic pump, gas dryer means, make-up gas mixing means and gas metering means.

In a further aspect, the invention provides a computer-based control system for operating the monitor.

Other and further features, advantages, objects, variations, and the like will be apparent to those skilled in the art from the present disclosure taken with the accompanying drawings and appended claims.

BRIEF DESCRIPTION OF THE DRAWINGS

In the drawings, which comprise a portion of this disclosure:

FIGS. 8A, 8B and 8C show diagrammatic views in side elevation of laminar flow gas flow sensing devices employed in the apparatus of FIG. 7;

FIGS. 9A and 9B comprise a flow diagram of one embodiment of a computer program suitable for operating the monitor apparatus of FIG. 7 wherein FIG. 9A is the program used for monitor device calibrating, and FIG. 9B is the program used for monitor device sampling;

DETAILED DESCRIPTION

Figure 2:
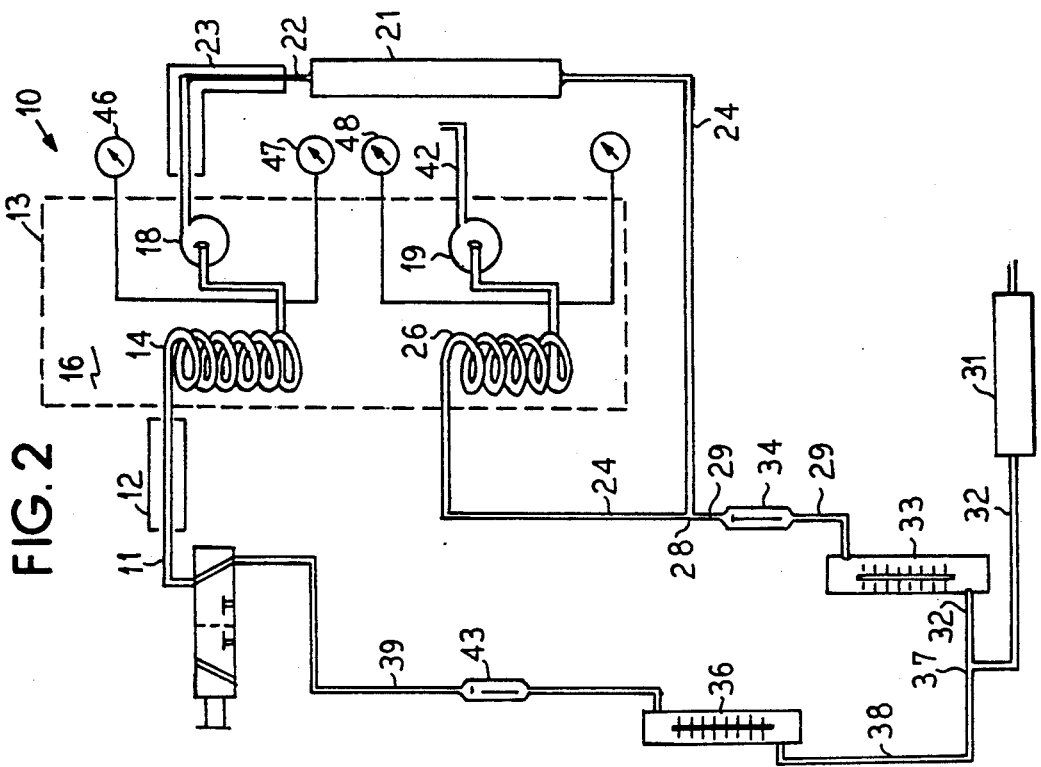
FIG. 2 is a diagram similar to FIG. 1, but showing the embodiment configured for calibrating.
Figure 1:
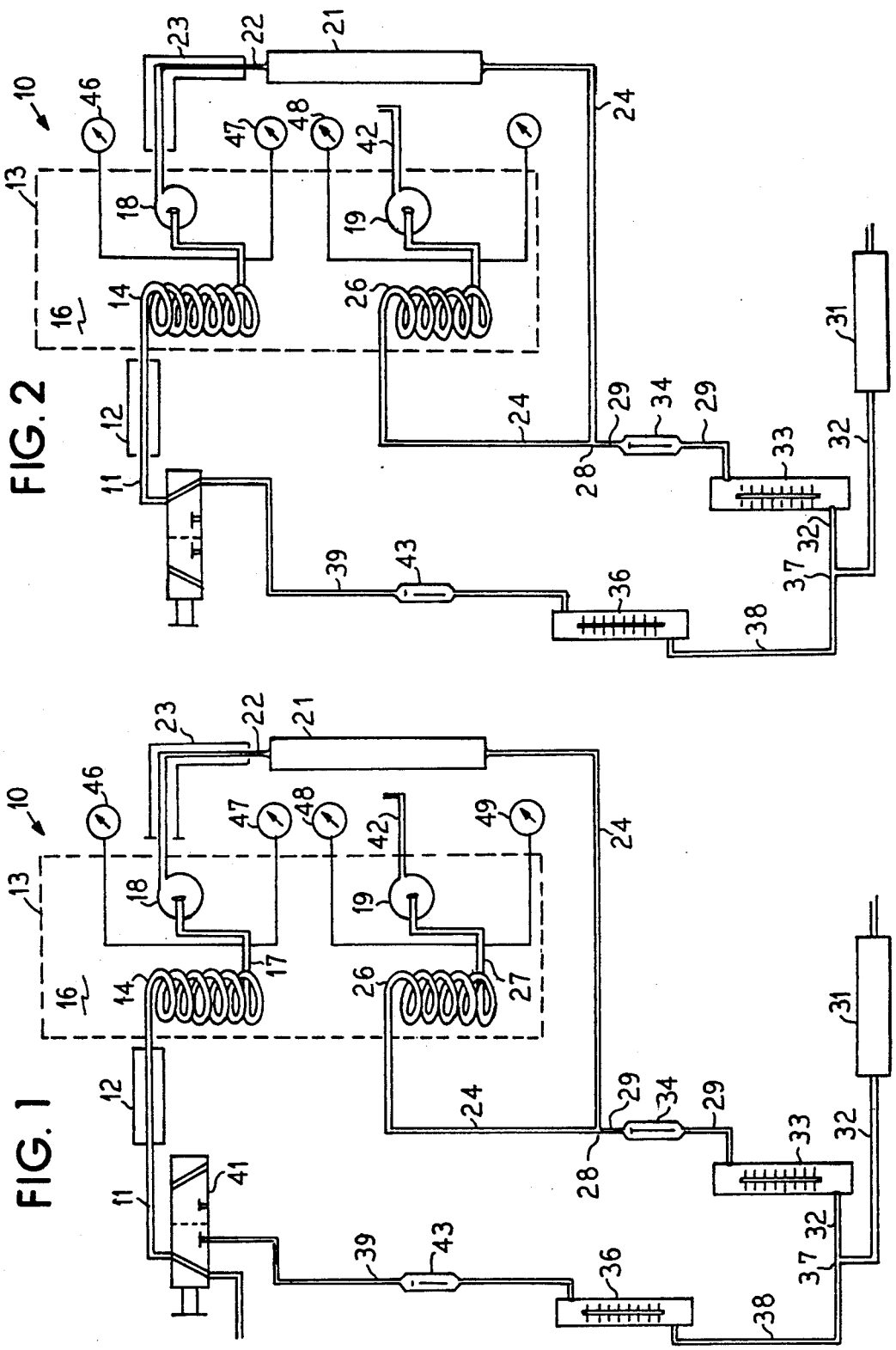
FIG. 1 is a simplified schematic-type diagram of one embodiment of a gas monitor according to the present invention which is adapted for moisture analysis.

Referring to FIGS. 1 and 2, there is seen one embodiment of a gas monitor apparatus according to this invention that is identified by the numeral 10. Monitor 10 is adapted for operation as a continuous monitor for moisture analysis of a sample gas stream that is continuously taken from a stack gas or the like.

FIG. 1 shows the moisture monitor 10 in its continuously operating sampling mode. In FIG. 1, a stream of non-condensed sample gas is admitted to monitor 10 through tube 11, which is preferably at least partially jacketed with a conventional electric tube heater 12.

The temperature at which heater 12 is set to operate is influenced by the temperature characteristically associated with an entering gas stream. In general, the heater 12 should have an operating temperature which is above the moisture condensation level of the entering sample gas. A suitable temperature for heater 12 can extend over a wide range with the lower end of the temperature in this range being above the boiling point for water at the pressure of the continuously entering sample gas stream. The upper end of the temperature in this range is preferably the decomposition limit of any gases present in the stream.

For example, when the entering sample gas is drawn from a stack gas which is at about atmospheric pressure and which has a characteristic temperature in the range of about 130° to about 350° F. (about 54° C. to about 177° C.), the heater 12 can have an operating temperature in the range of about 250° F. to about 350° F. (about 121° C. to about 177° C.).

Those skilled in the art will appreciate that a probe (not shown) for a gas to be sampled can comprise a conventional structure such as known to the prior art. Typically and preferably, such a probe includes a conventional filter (not shown) to remove coarse particulates, such as particulates having an average particle size above about 30 microns or the like. Since the present device employs a peristaltic pump, finer particulate filtration is not necessary because that type of pump continues to operate even with such particulates being present. Also, a probe may include a conventional liquid water separator (not shown) to remove any liquid water that may be present in the gas being sampled. Liquid water, if not removed, could enter the probe at the temperature of the gas being sampled. For example, the gas being sampled may be associated with a wet scrubber or the like.

Figure 6:
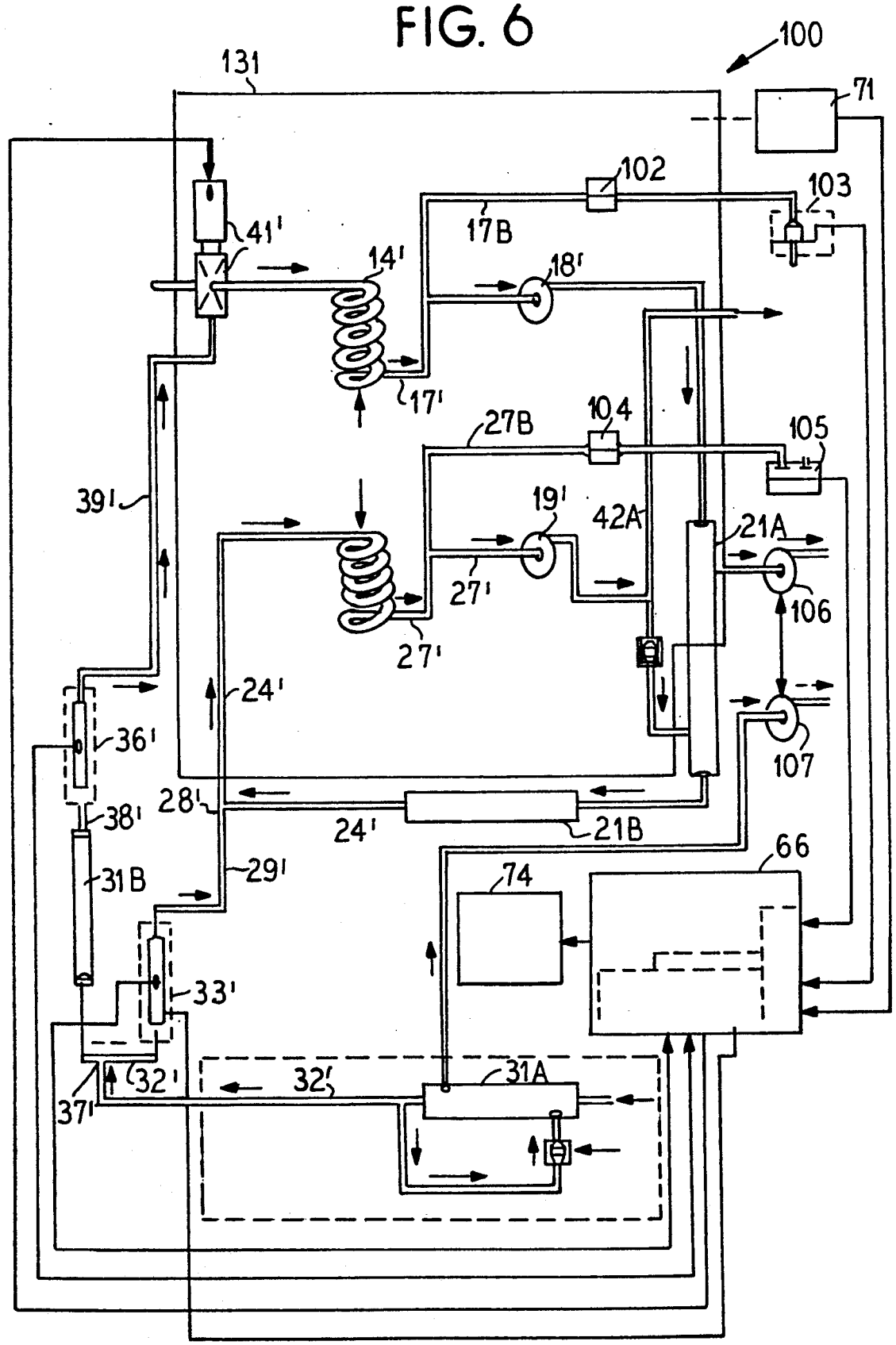
FIG. 6 is a diagram similar to FIG. 5 but showing the FIG. 5 embodiment configured for calibrating.

Tube 11 enters an electrically heated box 13 and is connected with a heat exchange coil 14 through a 3-way valve 41. Coil 14 is conveniently comprised of stainless steel or the like. Heated box 13, as shown, for example, in FIG. 6, is an enclosed heated structure Thus, a sample gas passing through valve 41 is uniformly heated in coil 14 to a temperature which corresponds to the temperature of the interior chamber 16 of box 13.

The temperature control means for box 13 is preferably provided with an adjustable set point for the desired temperature to be maintained in chamber 16. A set temperature within a wide elevated temperature range can be employed The lower end of this temperature range should be above the dew point for water at the particular sample gas pumping pressure being employed. The upper end of this temperature range is not critical and is conveniently chosen to be compatible with the equipment being used. A presently preferred set temperature for chamber 16 when measuring, for example, a stack gas, is in the range of about 200° F. to about 225° F. (about 93° C. to about 107° C.), and a presently most preferred set temperature is in the range of about 200° F. to about 205° F. (about 93° C. to about 96° C.). However, the monitor of this invention can be used in other applications; for example, a monitor embodiment can be used for measuring at ambient operating temperatures the carbon dioxide issuing from fermentation tanks.

A resulting uniformly heated sample gas passes from coil 14 through a relatively short lead tube 17 into one head 18 of a twin headed peristaltic pump (not detailed). Any convenient commercially available peristaltic pump with substantially identically rated twin pumping heads 18 and 19 that are driven through a common drive draft can be used. One presently preferred peristaltic pump is a "Masterflex L/S" model Lexan/cold rolled steel obtained from the Cole Parmer Co. of Chicago, Ill. Both pumping heads, that is first head 18 and the other (second) head 19 (whose usage is hereinbelow explained), of the peristaltic pump are positioned within chamber 16. Thus, both heads 18 and 19 are maintained at the identical set temperature of chamber 16. Each of heads 18 and 19 is thus adapted for pumping gas at the same volumetric flow rate.

Various pumping rates can be employed for the heads 18 and 19 within a wide constant volumetric flow rate range. A present preference is to employ a volumetric pumping rate for each head 18 and 19 that is in the range of about 0.2 to about 2.0 liters per minute (1/min), and a presently most preferred pumping rate is about 0.25 1/min). As used herein, the term "flow" refers to the volumetric pumping rate.

From pump head 18, sample gas is delivered through an output tube 22 to a dryer 21. Tube 22 is conveniently jacketed by a conventional electric tube heater 23 to maintain the heated and pumped sample gas in tube 22 above the condensation temperature of any water vapor (moisture) therein. The tube heater 23 can be, for example, similar to tube heater 12. As those skilled in the art will appreciate, sample gas exiting head 18 need not be maintained at the same temperature as that achieved in chamber 16. Thus, it is sufficient for present purposes if sample gas in tube 22 is maintained by heater 23 at, for example, a temperature in the range of about 200° F. to about 350° F. (about 93° C. to about 177° C.). A present preference is to employ a temperature in the range of about 250° F. to about 300° F. (about 121° C. to about 149° C.).

For temperature regulation of heaters 12 and 23, it is convenient to employ a self-limiting power supply line. Such a line is preferably provided with a heater that has a negative temperature coefficient resistance element, that is, an element where the resistance increases with increasing temperature. The line is thus selected to operate over the range of the preselected temperature, and the line itself controls heaters 12 and 23 at the preselected temperature.

The term "dryer", "drying" or the like as used herein in reference to water vapor separation from a sample gas indicates removal of water vapor by any means or technique, including condensation, absorption, adsorption, chemical reaction, or the like.

While any convenient dryer structure or type can be used, the dryer 21 in monitor 10 is preferably of the tube type so that, during continuous passage of sample gas therethrough, drying is accomplished. The dryer 21 should function to remove completely all moisture vapor present in the sample gas.

One present preference is to employ a so-called membrane dryer, such as a "Perma Pure" dryer which is available from Perma Pure Products, Inc. of Toms River, N.J. Such a dryer utilizes a hygroscopic, ion exchange membrane in a continuous drying operation to selectively remove water vapor from mixed gas streams. The membrane is an extrudible desiccant in tubular form. Either a single tube or a bundle of tubes with a common header is formed into a tube configuration, and the configuration is sealed into an impermeable shell which has sample inlet product outlet openings.

In dryer 21, when a wet gas stream flows through the tubes and a countercurrent dry gas stream purges the shell interior, water vapor molecules are transferred through the tubing walls. The wet gas is dried, and the dry purge gas becomes wet as it carries away the water vapor. The wet purge gas exits on the shell side at a purge outlet. The water vapor is usually vented to the atmosphere. The dryer temperature is kept above the sample dew point during a drying procedure to prevent condensation. One desires the membrane dryer temperature to be above whatever the dew point of the gas is at that physical location in the dryer. Using a temperature in the above indicated range, the gas will dry from an anticipated maximum dew point of 180° F. to a dew point well below ambient.

Another present preference for a dryer 21 is to employ a sequential combination of a loop membrane dryer with a canister (or bed) charged with "Drierite" or a like particulate desiccant through which the sample gas is successively flowed. "Drierite" is a trademark of the W. A. Hammond Drierite Company for a special form of commercially offered anhydrous calcium sulfate having a highly porous granular structure and a high affinity for water. This material absorbs water vapor both by hydration and capillary action.

Some form of indicator (not shown) signaling desiccant exhaustion for a canister is preferred so one can tell when to change it. Virtually any other desiccant or drying agent can be used such, as silica gel, indicating silica gel, molecular sieves, or the like. It is now preferred for a drying agent to have an expected removal efficiency such that gas dried therewith has a dew point not greater than about −20° F.

The resulting dried sample gas issuing from the dryer 21 enters a delivery tube 24 and is conveyed back into box 13. Tube 24 connects in chamber 16 with another heat exchange coil 26 that (like coil 14) is also comprised of stainless steel or the like. Gas passing through coil 26 is uniformly heated to the temperature at which the interior chamber 16 of box 13 is maintained. The resulting uniformly heated sample gas passes from coil 26 through a relatively short lead tube 27 into the second or other head 19 of the peristaltic pump.

Before it enters the box 13, the tube 24 is fitted with a T-connector 28 through which a make-up gas that is charged through an interconnecting tube 29 is admixed with resulting dehydrated sample gas flowing in tube 24. While any convenient gas which is non-reactive with the resulting sample gas can be employed as the make-up gas, it is presently convenient and greatly preferred to employ dried air as the make-up gas. Those skilled in the art will appreciate that any noncondensing, invariable, nonreactive gas can be used quite effectively.

It is presently preferred to use dry air as the make-up gas because: 1) By having all the gas that exits the second pump head dry, it can be used as the purge gas for the loop membrane dryer. This provides better drying than if ambient air is used as the purge gas for the membrane dryer. 2) Dry gas of some type is needed for the "zero" calibration operating mode of monitor 10 described hereinbelow. By keeping a second membrane dryer continuously operating in monitor 10, then dry air is available when needed for the "zero" calibration. Otherwise, a membrane dryer in reflux mode requires about 30 minutes of operation before the air it is producing is dry enough to be used effectively as a "zero" calibration gas. 3) If non-dried ambient air were to be used at this location, then the slight molecular weight and viscosity shift that occurs when the moisture content of air changes could affects the readings of both a laminar flow element type sensor and a true mass flow sensor. Use of dry air eliminates this problem. Preferably, the ambient air drawn for drying is preliminarily filtered (filter not shown) simply to keep a interior of the membrane dryer clean.

The T-connector 28 has no check valve because removal of moisture will always result in a reduction in volume in the loop. Therefore, gas will only flow into the T-connector 28 through line 29. The one possible exception to this result occurs during "zero" calibration where the volumes of the two operating pump heads are compared. During that sequence, the flow, either into or out of the T-connector 28 through line 29, needs to be determined, and that value and flow direction are included as a constant in the equations that the control computer uses to determine the volume of material removed during sample drying.

In practice, even when the monitor apparatus 10 is started up, the gas in the loop is "dry" so there is simultaneous flow of make-up air into the system through line 29 to replace the volume lost in the dryer means.

Thus, to obtain dried air, atmospheric (ambient) air is used. A dryer 31 is provided which is preferably operatable in the partial reflux mode. Dryer 31 is preferably exactly the same type of dryer as dryer 21, but it may have a different capacity. Preferably, a "Perma Pure" dryer (available from Perma Pure Products, Inc. of Toms River, N.J.) is employed as dryer 31 because it requires no change of drying materials. In such a reflux mode, a gas mixture from head 19 can be used for purging by passing it through the dryer. Compared to dryer 21 that removes moisture from stack gases that may contain up to about 50% by volume moisture, dryer 31 starts with relatively dry ambient air that characteristically contains no more than about 6.5% moisture by volume (which corresponds to a 100° F. day at 100% relative humidity). As a consequence, it is believed that a "Drierite" or like desiccant-charged canister is not required for use in combination with a "Perma Pure" type dryer, but can optionally be used, if desired.

From dryer 31, the dried make-up air is conveyed through tube 32 to a flow meter 33. The flow meter 33 measures either gas flow rate therethrough or the point velocity of gas passing therethrough. From such a measurement, the volume of the dried air passing therethrough is determined. "Flow rate" is the time rate of motion expressed either as fluid (gas) volume per unit time (volumetric flow rate) or as fluid (gas) mass for unit time (mass flow rate). Measurement of volumetric flow rate can be converted to mass flow rate by simultaneously measuring density and computing mass flow rate from the two measurements.

Suitable known flow-sensing elements which can be used include (a) differential-pressure flow sensing elements (where a differential pressure transducer has input ports connected across two points located at a restriction or curvature in a tube section and the transducer output is representative of a flow rate through the sensing element), (b) mechanical flow-sensing elements (where freely moving elements such as a turbine or propeller, or mechanically restrained elements, such as a float in a vertical tapered tube, a spring-restrained plug, a hinged or cantilevered vane, have a displacement deflection or angular speed that is proportional to flow rate), and (c) flow sensing by fluid characteristics (where transduction elements are designed and installed so that they interact with the moving gas and produce an output relative to flow rate). Any convenient or suitable flow meter known to the prior art can be used, as those skilled in the art will appreciate.

One present preference is to employ a mass flow meter as the meter 33; in particular, a so-called "true" mass flow meter which responds directly to mass flow rate or an inferential mass flow meter which commonly measures volumetric flow rate and gas density separately. A presently preferred mass flow meter is a "Top=Trak" series 820 mass flow meter which is commercially available from Sierra Instruments of Carmel Valley, Calif. which employs a straight sensor tube and a laminar flow bypass channel and wherein a measured resistance temperature differential is detected and gives an output signal that is directly and linearly proportional to gas mass flow. After passage through meter 33, the dried air enters tube 29 and passes therethrough to the T-connector 28.

Optionally but preferably, a flow restrictor 34 is placed in tube 29 downstream from meter 33 but before the T-connector 28 to dampen the flow pulses that are characteristic of peristaltic pumps, thereby enhancing accurate measurement and monitoring. A restrictor 34 is conveniently and preferably formed as a bore in a block or the like. The bore preferably has an adjustable orifice, and the inside diameter of the bore is smaller than the inside diameter of the tube 29.

Figure 3:
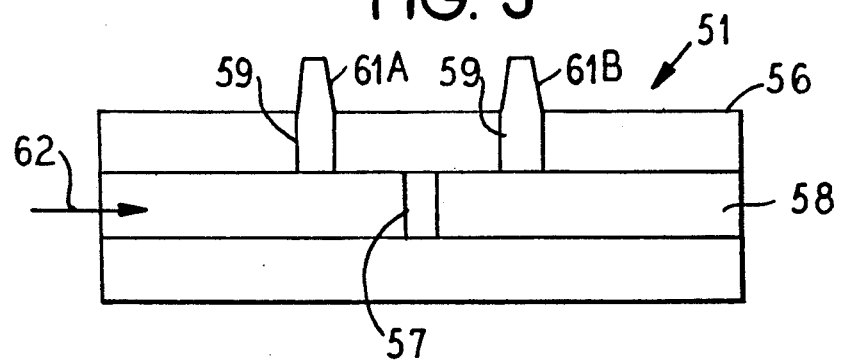
FIG. 3 is a longitudinal sectional view of a laminar flow device that is suitable for use as a flow meter in the gas monitor of FIG. 1.

Another present preference is to employ a laminar flow device 51 as the flow meter 33. The laminar flow device 51 can have a structure such as shown in FIG. 3 where device 51 utilizes a tubular housing 56 which is conveniently and preferably formed of a molded plastic, such as a polyamide, polyester, polyurethane, polycarbonate or the like. A porous filter disc or flow element 57 is mounted across the mid-region of a smooth walled cylindrical passageway 58 which extends through housing 56. The mounting is conveniently achieved, for example, by swaging disc 57 into an interference fit hole. Disc 57 is preferably comprised of a porous metal and can have, for example, a thickness in the range of about 1/16 inches to about ⅛ inches (in.) and a diameter which corresponds with the diameter of passageway 58, exemplary diameters being in the range of about ⅜ in. to about ½ in. A present preference is to employ a porous metal disc 57 which has a traverse gas flow characteristic that is in the range of about 5 to about 15 SCFM/ft² for a pressure drop of from 0 to about 10 in. H₂O across the disc. Suitable porous metal discs are commercially available, for example, from the Mott Metallurgical Corp. of Farmington, Conn.

Radially extending through the wall of housing 56, one on each side of the disc 57 and in longitudinally (relative to passageway 58) spaced relationship thereto, are a pair of apertures 59. The laminar flow device 51 is not an orifice meter. For a laminar flow device 51, the cross section of the flow path is very, very much smaller than the approach passage. In this case, for example, the pore size of the elements range from about 5 to about 100 microns (0.0002 to 0.004 inch) versus the interior approach diameter of about 0.375 inch or a minimum ratio of 1:100. The Reynolds numbers are also low in the laminar region. Because of this, the position of the upstream and downstream taps is unimportant.

Each aperture 59 is fitted with a pressure tap fitting 61 which is externally connected to a pressure transducer (not shown). Thus, when gas flow through passageway 58 occurs in the direction shown by arrow 62, the upstream fitting 61A delivers a pressure to an upstream pressure sensing transducer, and the downstream fitting 61B delivers a pressure to a downstream pressure sensing transducer. Such a differential pressure sensor is a single device where the anticipated positive pressure is placed on the front side of a diaphragm and the anticipated negative pressure is placed on the back side. The device registers the difference between the two pressures directly and does not require computation. If two different meters are used and the overall pressure in the system is large, then one is measuring a small difference in two large numbers, leading to unacceptable errors. The measured difference between the upstream and the downstream gas pressures as determined by the single differential pressure sensor is converted into volumetric or mass flow rate through comparison to a look-up table stored in the process control computer (as described below).

Figure 4:
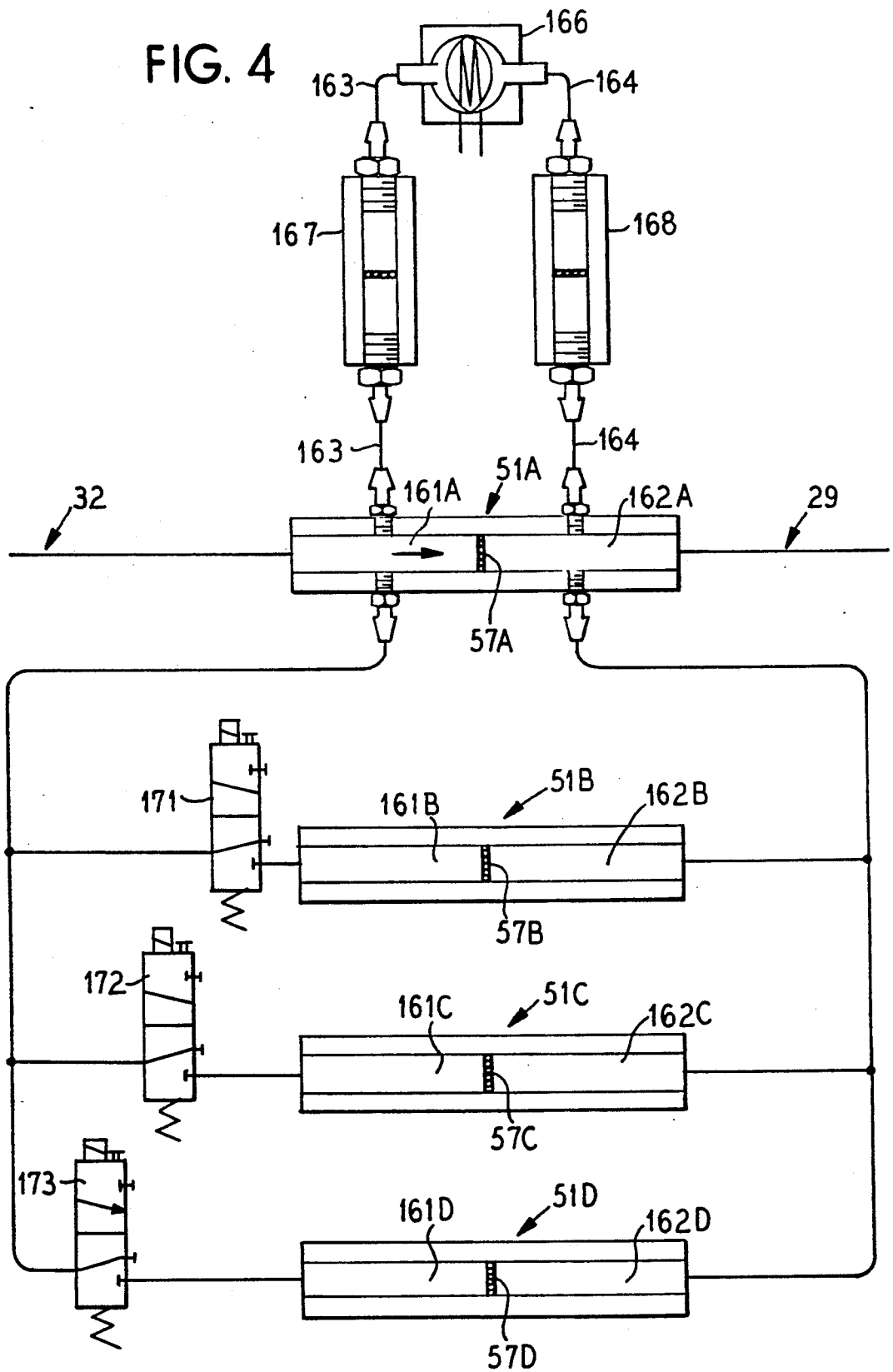
FIG. 4 is a diagrammatic view of one embodiment of a flow grid network that incorporates a plurality of laminar flow devices such as shown in FIG. 3 which network is suitable for use as a flow meter in the gas monitor of FIG. 1.

In order for such a laminar flow device 51 to accurately cover (i.e., measure) all possible flow rates of dried air which could be drawn into T-connector 28 from tube 29, a flow meter 33 can comprise a plurality of laminar flow devices 51 that are arranged in a grid network, such as illustratively shown in FIG. 4 where a flow grid 52 including four flow elements 51 is provided.

In FIG. 4, for convenience in identification, the respective laminar flow devices 51 are designated as 51A, 51B, 51C and 51D, respectively. In the laminar flow device 51A, each of the front side chamber 161A and the back side chamber 162A relative to the disc 57 are interconnected by respective tubes 163 and 164 to opposite sides of a differential pressure transducer 166. To dampen pulsations in air pressure, each of the tubes 163 and 164 has functionally interposed therein a snubber 167 and 168, respectively.

Each of the laminar flow devices 51B, 51C and 51D is connected in parallel with device 51A. Thus, the respective front side chambers 161B, 161C and 161D of devices 51B, 51C and 51D are connected through the illustrated connecting tube and T-connectors shown in FIG. 4 to the back side chamber 162A. However, just before each of the connecting tubes for the respective front side chambers 161B, 161C and 161D join with such chambers, a valve 171, 172 and 173, respectively is functionally interposed. For low operating pressures, each of the valves 171, 172 and 173 is closed. When the operating pressure exceeds a first predetermined higher pressure, valve 171 is opened. When the operating pressure next exceeds a second and higher predetermined pressure (relative to the first pressure) valve 172 is also opened. When the operating pressure next exceeds a third and higher predetermined pressure (relative to the second pressure), valve 173 is also opened. When the front side chambers 161B, 161C and 161D are opened, then the associated respective back side chambers 162B, 162C and 162D are connected to back side chamber 162A via the interconnecting tubes and T-connectors. Thus, increases in operating pressure are distributed among the flow devices 51A, 51B, 51C and 51D, and differential pressure measurements using transducer 166 across the filter disc 57A never become a small difference between two large quantities, as desired.

Monitor apparatus 10 is preferably computer controlled. A control computer sequence for operating the valves is preferably quite simple. For example, with all the valves 171, 172 and 173 "off", the lowest flow device is in place and is active at all times. The normally expected maximum differential pressure across this device is about 10 in. water. When a substantial signal of 9 in. water is encountered, the control computer opens the first two-way solenoid valve 171 which drops the pressure to about 2 in. water as the next laminar flow element is added in parallel to the flow monitoring system. As the flow continues to rise to another sustained 9 in. water, the control computer opens the next valve 172, and so on similarly through the third valve 173.

On the downside, a sustained pressure of 1 in. or below causes the control computer to deactivate the last solenoid activated valve 173, and the process is repeated until no additional valves 172 or 171 are operating. With each valve activation, the (internal) control computer program switches to the appropriate look-up table corresponding to whatever number of devices 51 are then connected in parallel. The correct pressure is then derived from the voltage output from piezo-resistive pressure transducer connected across each of the devices 51.

Thus, as can be appreciated from the foregoing description, the control computer starts with the lowest flow rate conducting flow element 51 in grid 52 to determine the anticipated moisture range and then signals a switch to however many flow elements 51 gives the greatest measurement accuracy without overpressuring the differential pressure transducer associated with that flow element 51. Unless otherwise indicated, valves used in this invention are preferably solenoid activated for remote control through a control computer or the like.

The use of the grid 52 is desirable because it allows the monitor 10 to be as accurate as possible throughout its full operating range. The grid 52 also reduces the costs associated with many other conventional structures which could be employed as a flow meter 33. Moreover, the grid 52 eliminates the need for flow restrictors 43 in the measuring lines to mitigate pump flow pulsations. When a mass flow sensor like the foregoing sensor made by Sierra Instruments is used, then a flow restrictor to dampen pulsations is necessary. However, when any differential pressure device (orifice, venturi, laminar flow element, multiple laminar flow elements, or the like) is used, then flow snubbers can be placed in the lines to the sensor rather than in the flow line.

For example, the elimination of flow restrictors is achieved in, for example, a grid 52 by placing flow snubbers 167 and 168 (see FIG. 4) in the differential pressure transducer lines. A flow snubber conveniently employs a centered metal disc such as is used in the laminar flow devices 51 except that such discs have a smaller pore diameter. Suitable such snubber discs are available commercially, for example, from Mott Metallurgical Corp.

As the dried sample gas from flow meter 33 passes through the T-connector 28, it draws make-up gas (in the embodiment shown, dried air) into the line 24. This is not an aspiration-like effect in the sense of an eductor pump aspirating material by converting velocity into suction. Thus, in FIG. 1, starting at pump head 18, pump heads 18 and 19 rotate together because they are on the same shaft; they are identical pump heads and therefore are supposed to each have the same pumping volume. Following the output from pump head 18, through line 22, through the dryer 21, through line 24, through preheater 26, through line 27 to pump head 19, one notices that there are no entrances or exits for the gas except T-connector 28 and dryer 21. If it is supposed that the gas is completely dry and the pump heads are exactly the same, then no volume will be removed from the gas loop by dryer 21, and therefore no gas will flow into the loop from line 29 through T-connector 28 because the system volume is mechanically fixed. For an invariant temperature and pressure system (which is why the heated box 13 is preferably used), the volume balance equation is basically: Volume in−Volume out=volume accumulated. In all cases, no volume is accumulated because the system volume is mechanically fixed; in this case, no water volume was removed by the dryer so no make-up air volume was required to keep the volume the same. In the case where water is present, Volume in=air+water vapor; Volume out=air+make up air of the same volume as the water vapor removed by the dryer. Again, volume accumulated=0 for a fixed volume system operating at a consistent temperature and pressure.

The resulting mixture of make-up gas and dried sample gas formed at T-connector 28 is thus fed through line 24 and into chamber 16 for heating in coil 26. The resulting heated mixture then passes into pump head 19 where the volume of gas which is pumped therethrough during pumping is equal to the volume of gas which passes through pump head 18 in apparatus 10.

The amount of make-up gas which is thus drawn into and flows through tube 24 via T-connector 28 from tube 29 is equal to the volume of the moisture that was removed from the sample gas in the dryer 21. As can be appreciated from the above description, apparatus 10 is a constant volume system. Although this condition may be somewhat difficult to maintain without a box 13, since any change in temperature or pressure causes gas volumes to change, this condition is inherently necessary since pumps are volume devices, not mass devices. Correspondingly, a constant and consistent temperature is maintained between pump heads in chamber 16. To mitigate the pressure factor, the pressure of the gas entering each pump head 18 and 19 is preferably monitored so that calculations can correct for any variations between the pressures at each location. Thus, the term "amount" as used herein always means "volume" unless otherwise indicated. Hence, the flow and the amount of make-up gas measured by meter 33 represent the actual volumetric amount of water vapor present in the sample gas that originally entered monitor 10 through tube 11.

As indicated, the effluent gas stream from head 19 can be conveyed by tube 42 to the shell side of a membrane type dryer and used as purge for at least a part of dryer 21 before such gas stream is vented to the atmosphere.

In order to calculate the moisture content of the incoming sample gas in tube 11, the flow through both pump heads 18 and 19 as well as the make-up air flow must be determined. The overall flow and variation in pump head volumes is readily determined by periodically placing the monitor 10 in a zero operating or calibrating mode. Such a mode can have a configuration such as shown in FIG. 2. For this zero mode, a three-way valve 41 that is preferably solenoid actuated (for remote control purposes) is connected across tube 11. Valve 41 also is connected to the terminus of a tube 39. Valve 41 is turned to block (that is, shut off) gas sample entry and flow through tube 11 and to allow instead metered dry air from tube 39 to flow successively through both pump heads 18 and 19.

To accomplish this result, a T-connector 37 is functionally mounted in tube 32 so that, at T-connector 37, the air flow divides with approximately half thereof going on forward in tube 32 to flow meter 33, and the other half thereof entering a tube 38. Since there is a T-connector in the line, in the non-zero mode all the flow goes to tube 32 while in the zero mode, the bulk, if not all, flows through tube 38. From the foregoing description, it will be appreciated that if the pump heads are actually identical, then no air will flow through tube 32 and meter 33 since the equal volumes will not require or reject any additional flow through meter 33.

The tube 38 delivers dried air to a flow meter 36. For reasons of convenience and accuracy of flow measurement, flow meter 36 can preferably have about same structure as flow meter 33. Because the flow rate of dry air as the sample gas feed, through tube 38 is uniform and consistent, the flow meter 36 can be comprised of a single laminar flow device 51 or mass flow meter.

From flow meter 36, dried air flows though tube 39 and is delivered to the three-way valve 41. A flow restrictor 43 is optionally but preferably placed in tube 39 between meter 36 and valve 41 for purposes similar to those explained above with reference to flow restrictor 34. Flow restrictor 43 can, and preferably does, have a structure that is similar to that of flow restrictor 34.

Since the zero mode uses dry air as the sample gas feed, the make-up air flow meter 33 displays the mechanical difference in the flows through the respective two pump heads 18 and 19. In the zero mode, the overall sample gas volume flowing into the first pump head 18 is measured by the second or dry air flow meter 36.

If desired, the zero mode can be achieved and practiced with a make-up gas other than dry air, as those skilled in the art will appreciate.

In operation, the moisture content of the sample gas entering tube 11 is determined by dividing the volumetric flow rate of the make-up air through tube 29 by the overall sample gas volume flow rate entering the first pump head 18, with adjustments for any mechanical differences determined while in the zero mode. The temperature and pressure of the sample gas and the zero gas are measured by conventional devices 46, 47, 48 and 49 prior to entry into each of the heads 18 and 19 of the peristaltic pump. For example, device 46 can be a pressure gauge, device 47 can be a temperature sensor such as a thermocouple, device 48 can be a thermocouple, and device 49 can be a pressure gauge. Corrections are made for any variations caused by those parameters. Since both flow meters 33 and 36 measure only dry air, flow therethrough can be equated with volume flow at consistent temperature and pressure.

In apparatus 10, the sample gas leaving pump head 19 is used in the membrane dryer, not because it is heated, but because it is dry. Dry air is desired as a purge gas for the presently preferred type of dryer used.

Another and presently preferred gas monitor embodiment of this invention as shown in FIGS. 5–9 and is designated for convenience herein by the numeral 100. The operation of monitor 100 is similar to monitor 10, and each corresponding component of monitor 100 is similarly numbered but has a prime (') mark added thereto for reference purposes.

In monitor 100, box 13' (see especially FIG. 7) has insulated walls 15 which are electrically heated by conventional electric resistance heating element 69. The chamber 16' is provided with a fan 68 whose drive shaft 175 extends through a portion of wall 15 (in association with appropriate bearing means, not shown) for functional association with an external drive motor 176 (see FIG. 7). Air circulation in chamber 16' is preferred so that all internal surface portions of box 13' and all components in chamber 16 are maintained at a constant and consistent predetermined elevated temperature. A conventional electronic temperature controller 71 is in functional association with a thermistor 70 or the like for achieving and maintaining a desired chamber 16' temperature. Temperature variations within chamber 16' or between components therein will cause measuring errors. For example, temperature variations between pump heads 18' and 19' of peristaltic pump 20, or associated incoming gas lines (not shown in FIG. 7, but see FIGS. 5 and 6) will cause errors in gas volume measurements.

Figure 5:
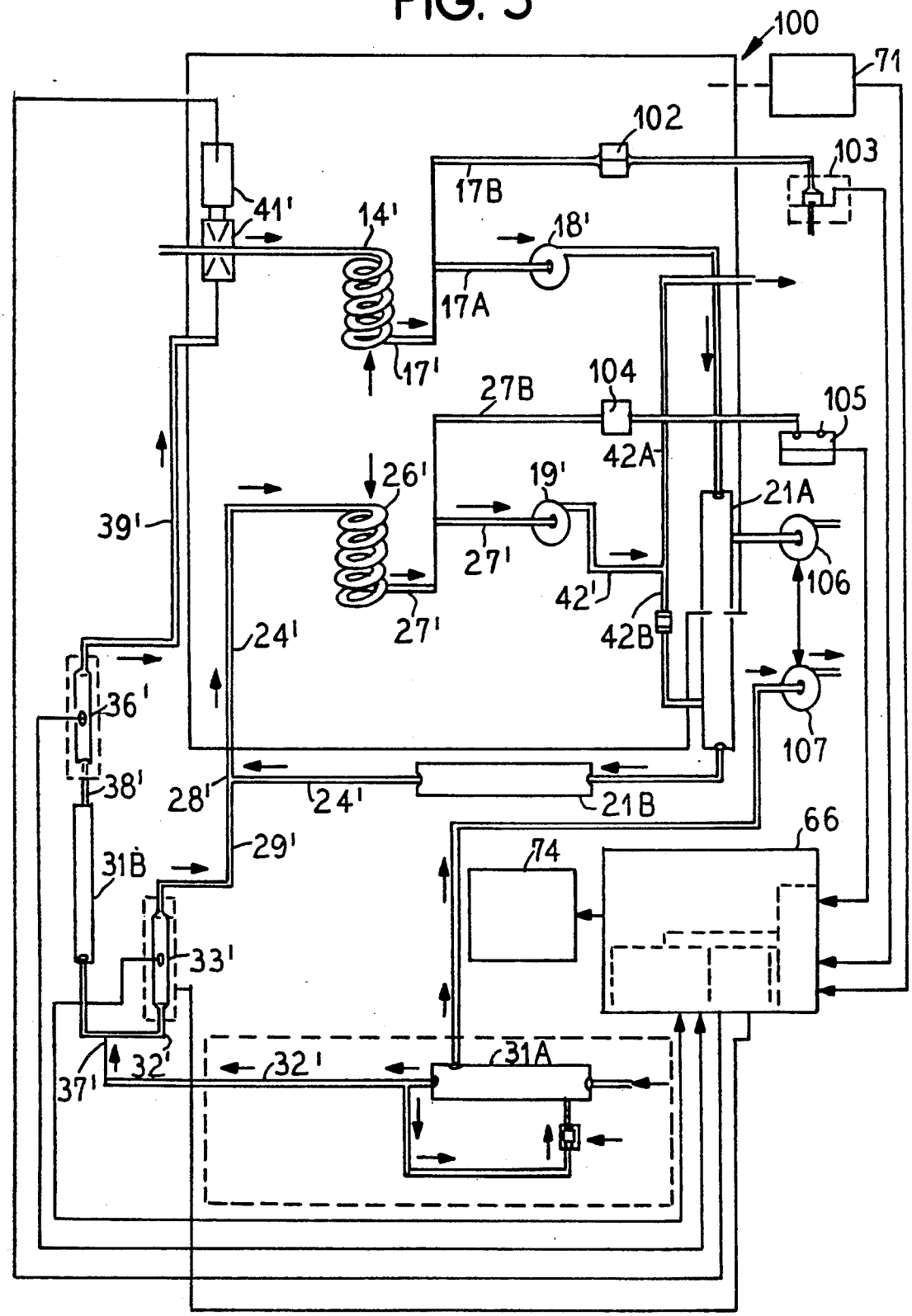
FIG. 5 is a schematic diagram similar to FIG. 1, but showing another and presently preferred embodiment of an inventive gas monitor.

The dryer 21 performance is influenced by the purge gas pressure inside the shell of the dryer. In general, by lowering the pressure inside the shell, the dryer 21 becomes more effective. Present information indicates this relationship to be about one degree dew point reduction for each inch of mercury pressure reduction. For example, if a dryer operating at ambient pressure (30 in. Hg.) achieves a sample gas dew point of $-20°$ F., then operating at a reduced pressure of 15 in. Hg. can yield a dew point of about $-35°$ F. As shown in FIGS. 5 and 6, in monitor 100, it is presently preferred to associate vacuum pumps 106 and 107 on the shell side of a "Perma Pure"-type dryer 21A and 31A, respectively, to achieve this added reduction.

In monitor 100, the dryer 21 can, if desired, be located so that about one half thereof is inside the heated box 13' and the remaining half is outside (as shown in FIGS. 5 and 6). With such a configuration, it is possible to eliminate the heater 23.

In monitor 100, as shown in FIGS. 5 and 6, the dryer 21 is comprised of a serial combination of a "Perma Pure"-type dryer 21A followed by a "Drierite"-type canister 21B, and the dryer 31 is likewise comprised of a combination of a "Perma Pure"-type dryer 31A and a following "Drierite" -type canister 31B.

The monitor 100 employs a similar structure for each of mass flow meters 33' and 36'. Thus, as shown in FIG. 8A, the meter 36' is a transducer-equipped device 110. Device 110 employs a generally tubular housing 111 which is conveniently formed of a molded plastic or the like and which has an axially extending bore 114 therein for passage therethrough of (in this apparatus) dried air, the direction of flow therethrough being shown by arrows marked in bore 114. Inset into and extending across bore 114 is a flow element 115 which can be comprised of sintered powdered metal or the like. A measuring tube 112 is provided which has a gas flow path as shown by the arrows along tube 112 and which has ingress and egress ports 116 and 117, respectively, axially perpendicularly formed in circumferential side wall portions of bore 114. As those skilled in the art will appreciate, no actual gas flow occurs through tube 112 in operation of device 110. The tube 112 is provided with an initial flow restrictor 118 which is mounted in the high pressure side of tube 112 and a terminal flow restrictor 119 which is mounted in the low pressure side of tube 112. Between the restrictors 118 and 119, the tube loop is associated with a differential pressure transducer 121. Various such transducers are commercially available, but a convenient transducer is available from Nova under the designation P/H NPH-8-002.5DH. Output from such transducer 121 is fed to a preamplifier 122 which with the transducer 121 is housed in a shielded box 123. The preamplifier output is fed to the control computer 66.

As shown in FIGS. 8B and 8C, the meter 33' is a transducer equipped device 125. Device 125 employs the housing 111 with its bore 114 and ingress and egress ports 116 and 117, respectively. Two flow elements 115 are employed in bore 114 in longitudinally spaced relationship to one another with one on each side of port 117. Before connecting with tube 29, gas exiting from bore 114 enters a connecting tube 126 which is itself first provided (relative to the direction of gas flow) with a three way solenoid activated valve 127 and is secondly provided with a T-connector 128. Port 117 is connected to valve 127 through a tube 129, and port 116 is connected to T-connector 128 through a tube 130. A flow restrictor 131 is provided in tube 130 so that in tube 130 between the restrictor 131 and port 116 a high pressure exists compared to the pressure in tube 130 between the restrictor 131 and connector 128. Between the flow restrictor 131 and the port 116, the tube 130 is associated with a differential pressure transducer 132. Thus, while gas flow occurs through bore 114 (the direction being shown by arrows marked in bore 114), no gas flow occurs in tube 130. The transducer 132 can be and preferably is the same as transducer 121. Output from such transducer 132 is fed to a preamplifier 133 which with transducer 132 is housed in a shielded box 134. The preamplifier output is fed to the control computer 66. Preamplifier 133 preferably has the same structure as preamplifier 122.

Device 125 thus functions to sense two different modes of make-up air flow. In the low flow volume mode as shown in FIG. 8B, tube 129 is closed by valve 127 so that gas (air) passes only though tube 126 and into tube 29. In the high flow volume mode as shown in FIG. 8C, tube 129 is opened by valve 127 so that gas (air) passes only through tube 129 and connects with tube 29 via T-connector 128. It is presently preferred that, in its deenergized state, the valve 127 places the device 125 in the configuration shown in FIG. 8B, and also that, in its energized state, the valve 127 places the device 125 in the configuration shown in FIG. 8C. In FIG. 8B with solenoid 127 deenergized (low flow volume operational mode), any given gas flow entering device 125 from tube 32 must pass through both flow elements 115 before reaching tube 29, thus creating a higher pressure difference across transducer element 132 than would occur with solenoid 127 energized. With solenoid 127 energized (high flow volume operational mode as shown in FIG. 8C), the same given gas flow only passes through one element, thus creating a lower differential pressure across transducer 132 than occurs when two elements restrict the flow (as in FIG. 8B above).

In either the high or the low volume operational mode, there is no flow of gas through the tube 130 which provides only pressure to each side of transducer element 132.

In monitor 100, pressure in line 17A is monitored through line 17B. Thus, a flow restrictor 102 is placed in line 17B before an interconnected pressure transducer 103 whose output is fed to control computer 66. Similarly, pressure in line 27' is monitored through line 27B. Thus, a flow restrictor 104 is placed in line 27B before an interconnected pressure transducer 105 whose output is likewise fed to computer 66.

Figure 9A:
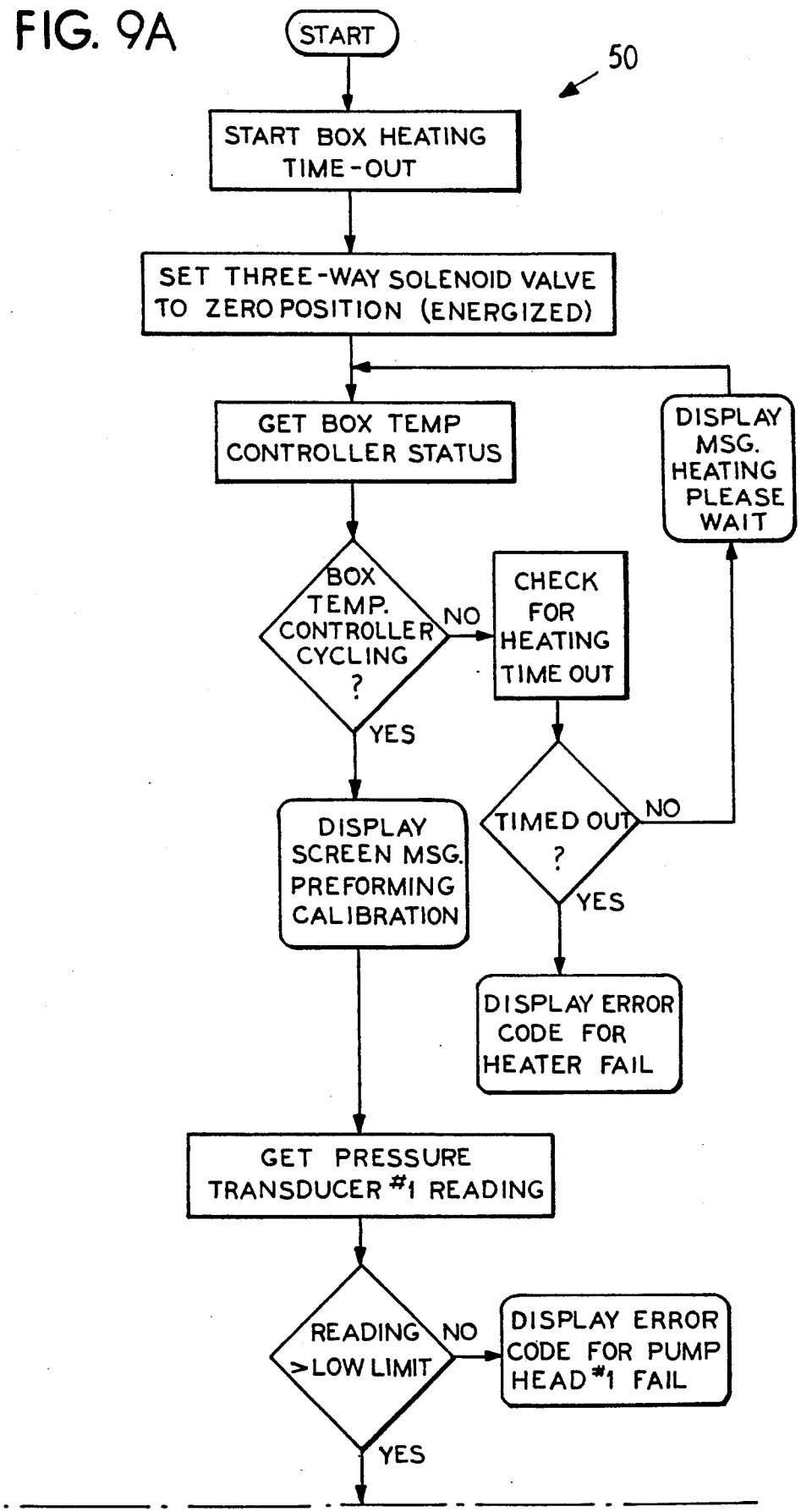
Figure 9A:
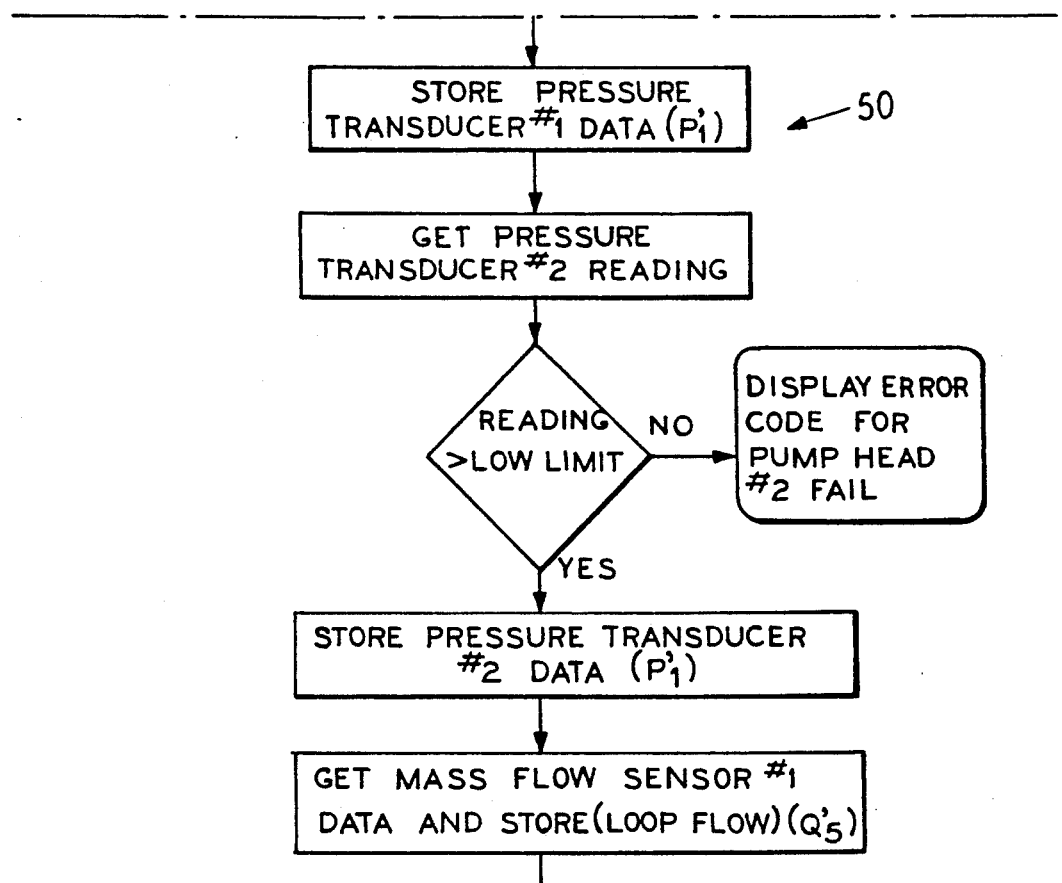
Figure 9B:
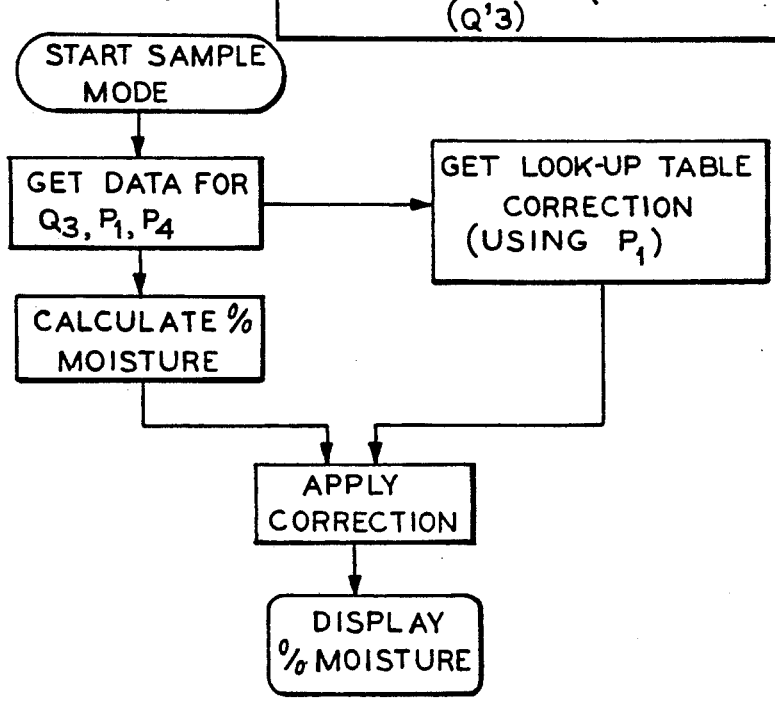

Operation including sequencing and control of the monitor 100 is preferably computer controlled. The functional operation of one embodiment of a computer software program 50 for operating the monitor 10 is shown in FIGS. 9A and 9B. FIGS. 9A and 9B are believed to be self explanatory to those skilled in the art.

Figure 7:
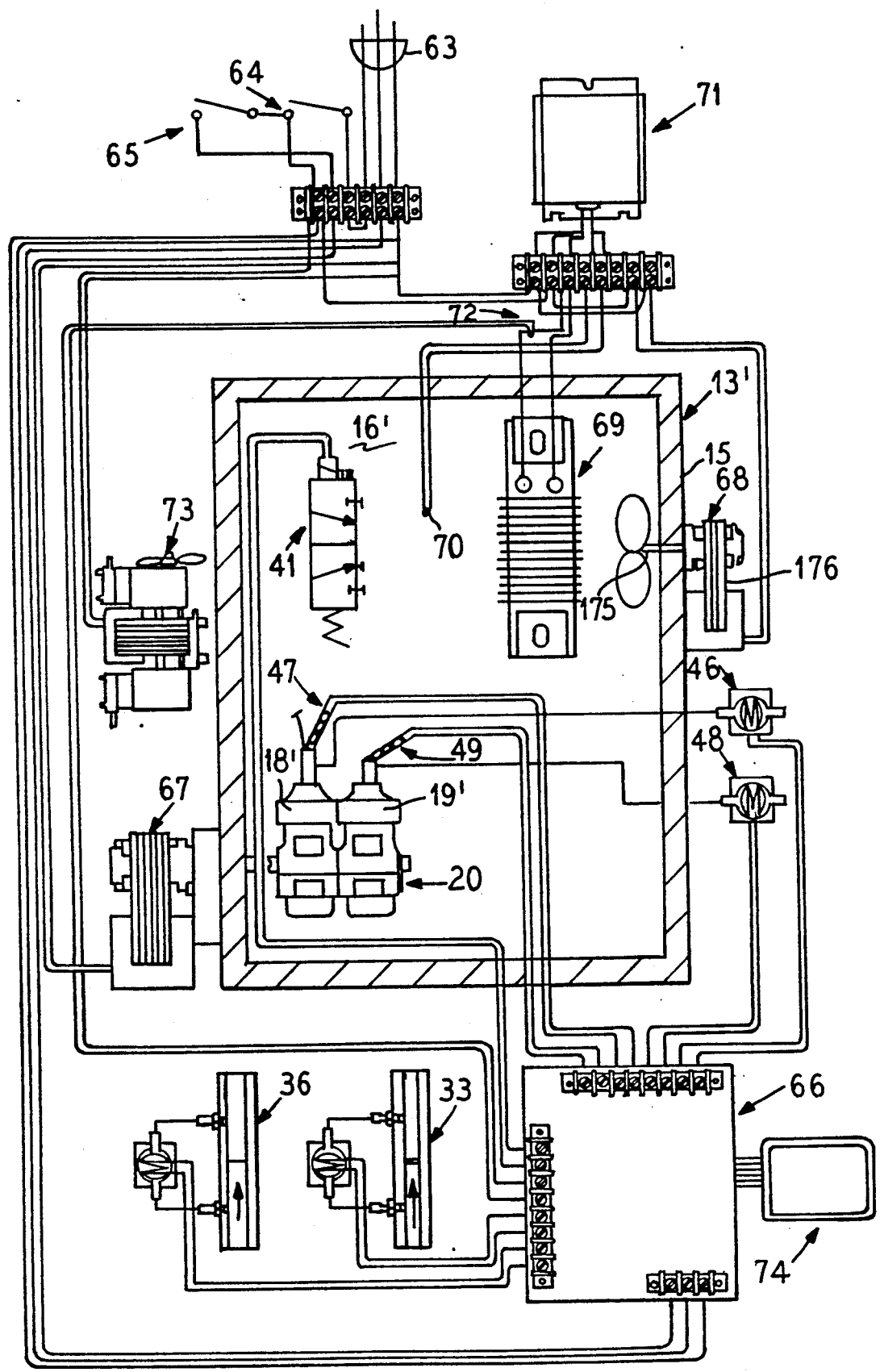
FIG. 7 is a layout of electrical interconnections for the gas monitor apparatus schematically diagrammed in FIGS. 5 and 6.

Referring to FIG. 7, incoming electrical power is supplied through a grounded plug 63. When master power is activated, power is supplied to control computer 66, fan 68, temperature controller 71, heating element 69, vacuum pump 73 and peristaltic pump motor switch 65. After application of power, temperature controller 71 supplies power to heating element 69 until thermistor 70 signals the temperature controller 71 that box 13 has reached a preset temperature. The control computer 66, using current sensor 72, determines if temperature controller 71 is cycling within a preset maximum timeout limit. If sensor 72 indicates that no current is flowing at initial startup, then an LCD display 74 outputs "HEATER FAILURE". The actual box 13' operating temperature is determined by the control computer reading of either temperature sensor 47 or 49 attached to the inlet to pump heads 18 and 19. Temperature current sensor 72 signals the control computer 66 that the set temperature is reached when the temperature controller 71 starts to supply varying amounts of power to the heating element 69. During this warm-up time period, the maximum set time limit for heating the box 13' is also checked. If the box 13' fails to reach normal operating temperature within this time limit, an error message code is displayed on the computer LCD display monitor 74 (FIG. 7) to indicate that the heating element 69 failed and the program progression is halted.

At this point, after the temperature has reached preset operational conditions, the operator can now turn on the peristaltic pump motor using switch 65. The reason that the pump motor is not turned on before the temperature has stabilized is that wet gas can condense in the interior of the lines going to the pump head 18' and in the cold membrane dryer 21A. Alternatively, a relay can be incorporated into the circuit so that the peristaltic pump motor cannot be turned on before the correct temperature is reached. Preferably, the peristaltic pump motor is not turned on automatically because the functional life of the tubing in the peristaltic pump is rotational time dependent. Having the tubing heated, but the pump not rotating, extends the time between tubing replacement. In some operating modes or equipment configurations, one may optionally actually stop the peristaltic pump motor periodically to increase tubing life.

When the temperature of box 13' reaches the preferred normal operating temperature (about 200° F. to about 225° F.), the software program issues a command to set the three-way Sample Mode/Zero Mode solenoid valve 41 (see FIGS. 5 and 6) to the zero position in preparation for calibration. A monitor 74 screen message is displayed to inform the operator that the system is in the calibration mode. The first stage (pump head 18') constant volume pump inlet pressure transducer 46 is read and the pressure data is compared to a stored predetermined minimum lower pressure limit. If the pressure is below the minimum pressure for normal operation, then an error code message is displayed on the monitor 74 to indicate possible pump head or pump motor failure, and the program progression is halted.

If pressure transducer 46 pressure data is above the minimum value, the data is stored for use later in the program. The identical steps are performed for the second 30 stage constant volume pump head 19' and the data is compared with the previously stored data for pressure for the first stage constant volume pump head 18' to determine any difference in pressure. This data is also stored in a memory location for use later.

The next step is to read the two meters 33 and 36 and to store data from each. Any difference in the flow rate is determined, and stored for use later as well.

The final step in the calibration or zero mode is to reset the three-way solenoid valve 41 to the "Sample" or normal continuous operation position and display a monitor screen message such as "SAMPLING MODE" or the like.

When electronics 66 are in the sampling mode, the display will read "SAMPLING MODE" and the percentage water in the sampled gas will be displayed as "XX.X% H2O". If a multi-element flow grid 52 (see FIG. 4 and preceding specification text thereon) is substituted for flow meter 33, then the electronics 66 monitors the output voltage from the flow grids differential pressure sensor 166 so that the number of operating laminar flow devices 51 in the grid 52 is maintained at an optimum number.

Those skilled in the art will appreciate that in place of a dryer 21A/21B of the absorbing or adsorbing types above indicated, one can employ a dryer which operates by moisture condensation at a controlled temperature or pressure or a combination thereof. Examples of suitable dryer structures include the temperature controlled, thermoelectrically cooled, flat plate heat exchanger manufactured by CAE/Exemplar of Carpinteria, Calif. and sold as model PEL-4. The unit essentially performs the same function as the other described dryers and is self-contained so no additional functions need be addressed.

Those skilled in the art will also appreciate that in place of such a dryer 21A/21B, one can employ an apparatus subcombination in monitor 100 which accomplishes a predetermined chemical or physical reaction of one or more predetermined components present in a sample gas mixture, thereby to remove predetermined components from a sample gas stream. The product or products of such a reaction can be solid(s), absorbable or condensable liquid(s) or the like, or a gas or gases having a greater or lesser volume than that associated with the starting separated components. Examples of suitable gas reactants include the solid material "Ascarite" (registered trademark of Arthur H. Thomas Co. sold by EM Science, Cherry Hill, N.J.) which can be placed in an absorbing canister for the removal of carbon dioxide from a gas stream passed therethrough.

The term "removing" or "removal" as used herein in reference to processing of a sample gas in a processing zone indicates the separation of a portion or component of such sample gas therefrom by any means or technique, including (a) condensation (for example, at a controlled temperature and/or pressure), (b) absorption or adsorption onto materials capable of removing the gaseous material of interest, (c) chemical or thermal reaction of a gaseous material of interest (thereby to convert such to a solid and/or absorbable or condensable material or a gas of a greater or lesser volume governed by a specific chemistry), or the like. Thus, "removing" results in a specific and reproducible volume change of a sample gas in a processing zone. Such a change in gas volume is measured by the instrument apparatus and method provided by the present invention.

Figure 10:
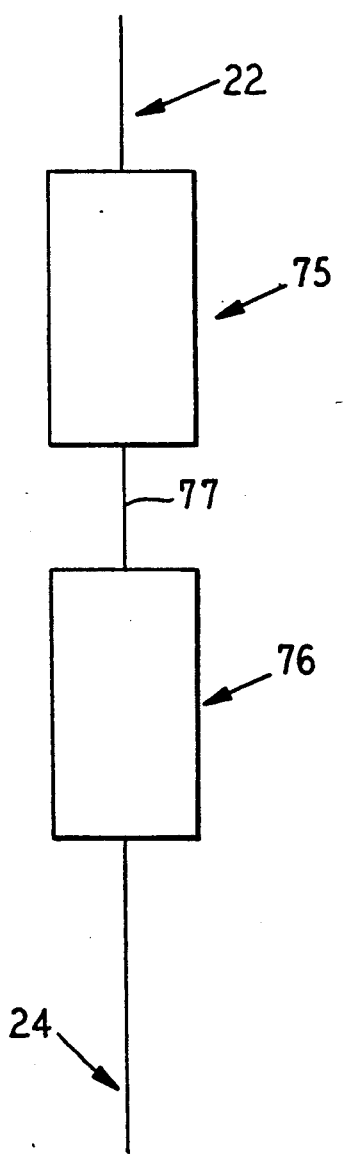
FIG. 10 is a block diagrammatic view illustrating an alternative (i.e., substitute) subassembly for dryer 21 in the embodiment shown in FIGS. 5 through 7.

Those skilled in the art will also appreciate that in place of a single function dryer 21A/21B one can employ in a monitor 100 a combination of a dryer and a reactor unit as shown in FIG. 10 so that more than one component of a sample gas is separated (i.e., removed) before a make-up gas (i.e., dried air) is admixed with the residual gas and metered to determine the total volume of the removed components. An embodiment of such a device which can replace dryer 21 in apparatus 10 is shown in FIG. 10.

As shown in FIG. 10, the dryer 21A/21B in monitor 100 (see FIGS. 5 and 6) is replaced by a series-connected combination dryer 75 and absorber 76 that is positioned between tubes 22 and 24 with the dryer 75 being interconnected to absorber 76 through a tube 77. Dryer 75 functions to absorb water vapor in the same manner described above for a canister dryer 21, and absorber 76 functions to selectively absorb a gas. For example, absorber 76 can be charged with "Ascarite" to remove carbon dioxide. Then, the combination of dryer 75 and absorber 76 removes both moisture and carbon dioxide from a sample gas that is passed therethrough.

Those skilled in the art will further appreciate that various embodiments of a monitor 100 can be provided. Each one of such employs a series of components in place of dryer 21A/21B. Each such component or subassembly adapted for successive removal of a different component or combination of gaseous components from a sample gas stream followed by addition to the residual stream of a make-up gas (i.e., dried air) to the residual gas stream for removed gas volume measurement in accord with the present invention. For example, a sample gas can comprise a mixture of at least three different component gases, and during the removing of predetermined components thereof, at least two components thereof are removed therefrom. Thus, a monitor apparatus 100 of this invention can be used to detect each one of a plurality of components existing in a sample gas. Illustrative subcombinations of apparatus for use with a monitor 100 in place of a dryer 21A/21B are shown in FIGS. 11, 12 and 13, which FIGS. are believed to be largely self-explanatory.

Figure 11:
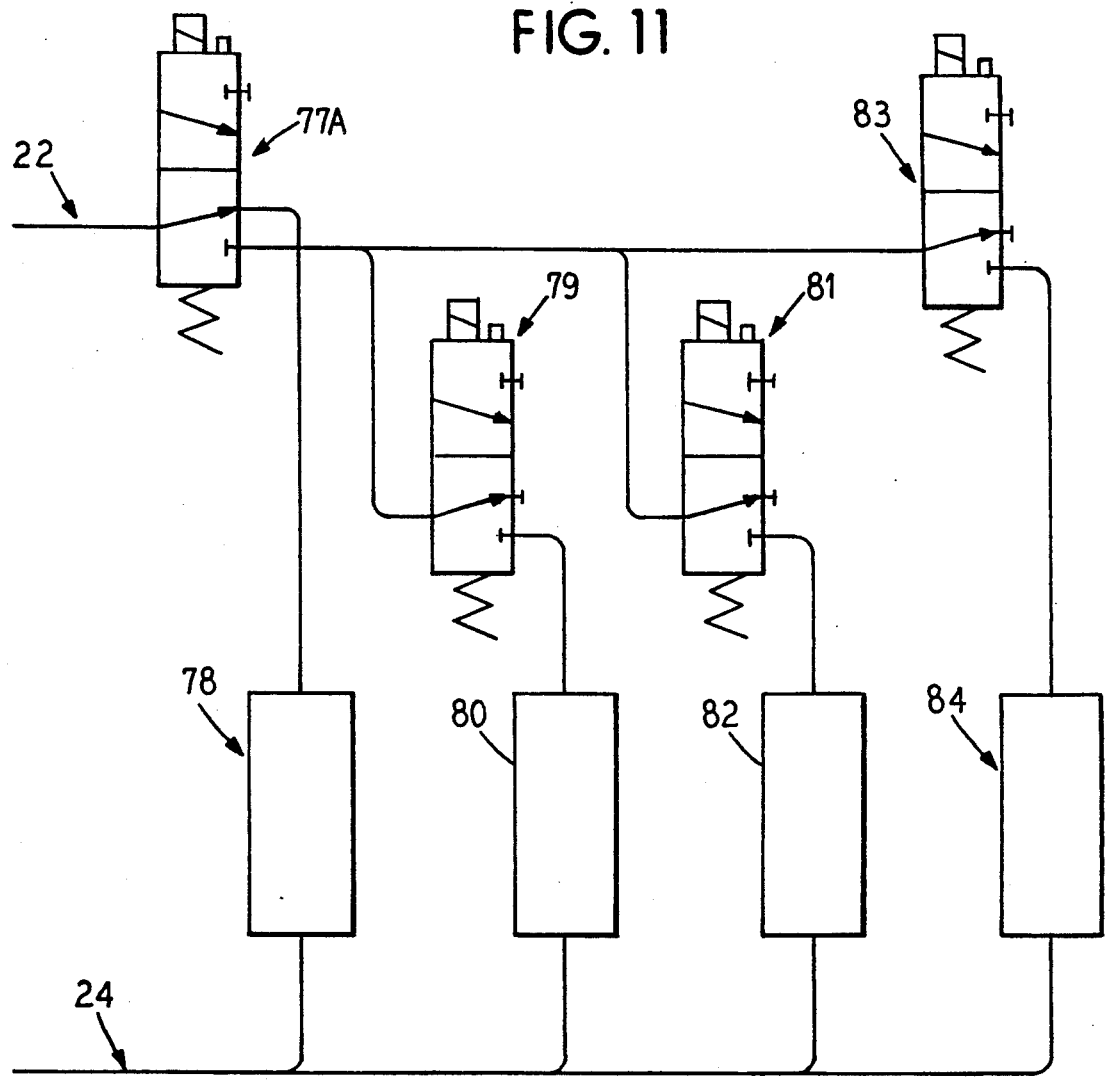
FIGS. 11, 12 and 13 are each a view similar to FIG. 10 but each showing further alternative subassemblies for dryer 21 in the embodiment shown in FIGS. 5 through 7.

The substitute subcombination for dryer 21A/21B shown in FIG. 11 provides capability for individual gas component measurement for each of four gas components. Thus, to measure all four gas components, the sample gas is fed in through line 22 past a valve 77A. In the open position shown, the sample gas passes through a water vapor dryer 78 (similar to a canister dryer 21) before entering tube 24. Next, dryer 78 is valved off by valve 77A and the sample gas enters a selected one of absorber canisters 80, 82 or 84 through appropriate setting of the interconnected valves 79, 81 and 83. Next, such selected one absorber canister of 80, 82, or 84 is itself valved off and sample gas enters one of the two remaining absorber canister by appropriate setting of the interconnected valves 79, 81 and 83. Finally, the second absorber is valved off and sample gas enters the third and last absorber canister through appropriate setting of the interconnected valves 79, 81 and 83. Each valve is valved into a desired predetermined programmed configuration by the control computer. After a short suitable stabilization period, the control computer 66 displays the name and the amount the material removed by the particular operating absorber canister.

Figure 12:
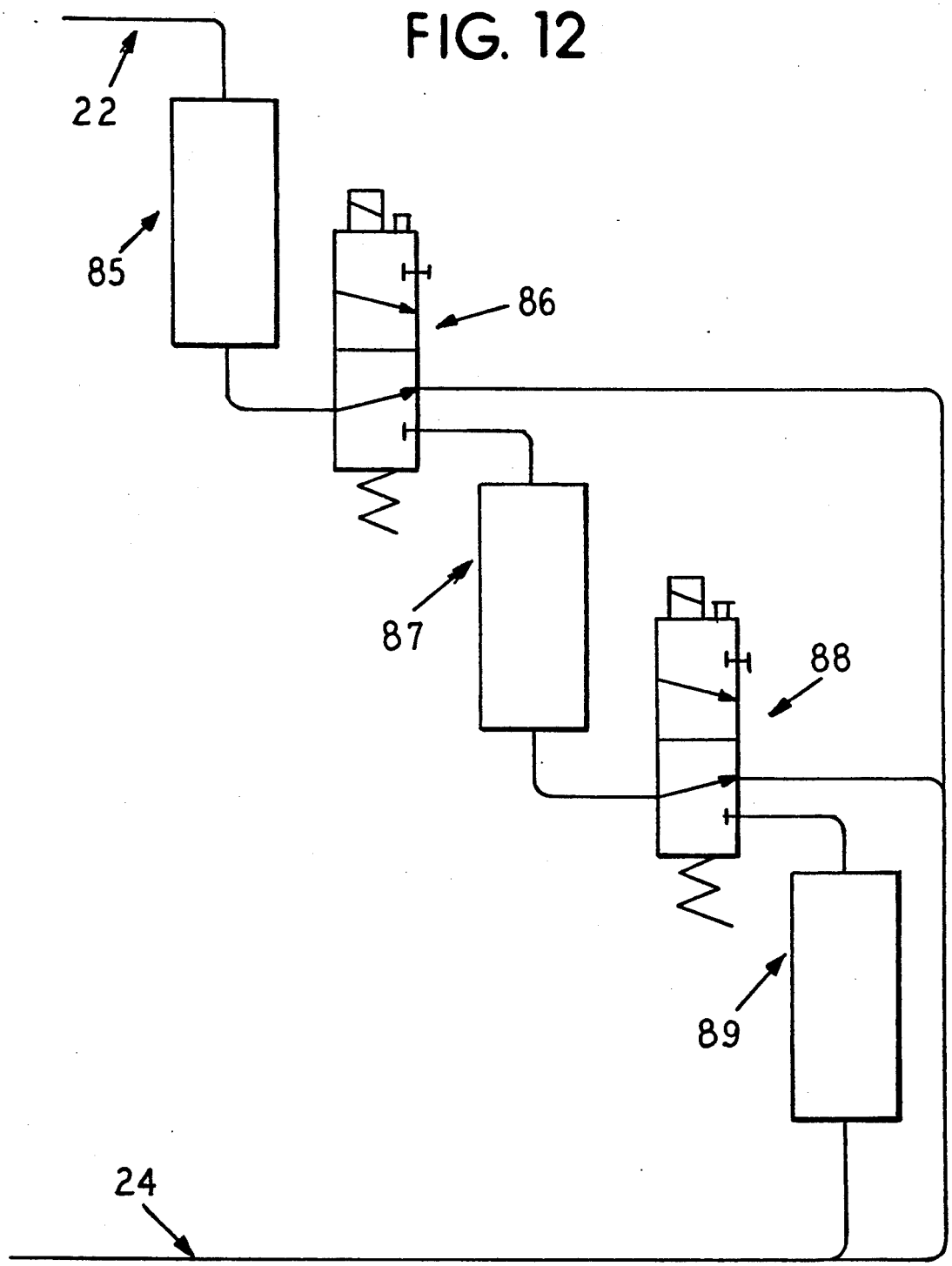

The substitute subcombination for dryer 21 shown in FIG. 12 provides a summation arrangement. Sample gas can pass selectively and progressively through a plurality of series-interconnected absorber canisters (here illustratively three) identified as 85, 87 and 89 with each absorber beyond the first (in relation to the progression of gas flow) being preceded by a valve identified here as 86 and 88 each of which is able to either permit gas passage therethrough to the subsequent absorber canister or permit circumventing (i.e., by passing) thereof. Each absorber canister is successively valved into a desired configuration by the control computer in accord with a programmed operating sequence. After a short suitable stabilization period, the control computer 66 displays the names of materials removed and the total amount of material removed by all absorber canisters in the series sequence.

Figure 13:
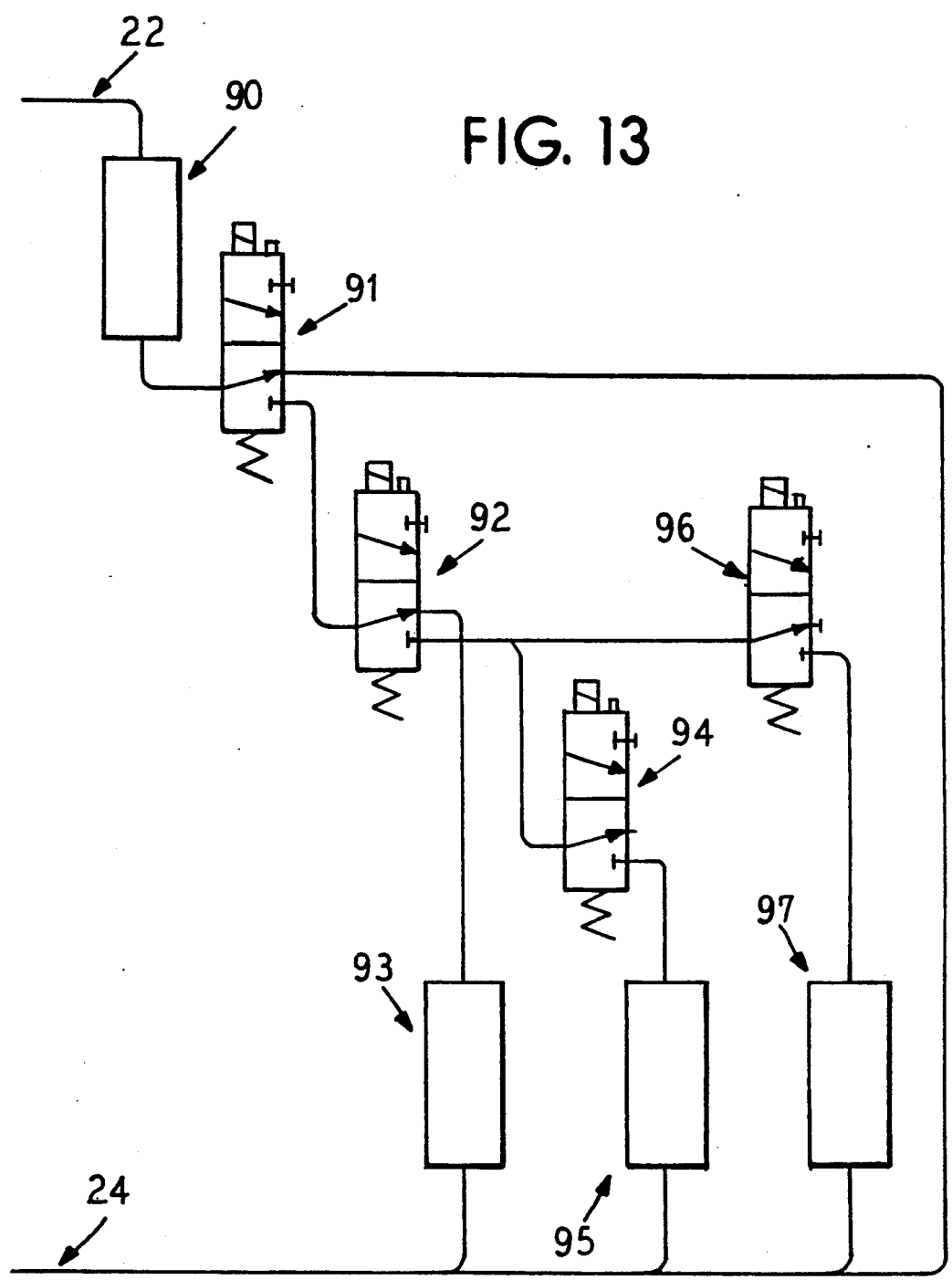

The substitute subcombination for dryer 21 shown in FIG. 13 provides an arrangement that converts the numerical output of gas removed by an absorber canister such as used in the FIG. 8 subcombination to a dry volume basis. Here, a moisture absorbing canister 90 is always in place to determine the moisture content which is stored in the control computer 66 as a reference. After the canister 90, each one of a plurality of absorber canisters, here shown as absorbers 93, 95 and 97, is valved into operation by the control computer 66 using valves 91, 92, 94 and 96. After a short suitable stabilization period, the control computer 66 displays the name and amount of material removed by that operating canister on a dry volume basis; the latter material in each instance being calculated by the control computer 66 with data stored when the apparatus was operating with only the dryer segment functioning. Such a switching back and forth between canister dryer 90 only and canister dryer 90 plus one absorber canister from among absorber canisters 93, 95 and 97 is computer controlled so that the moisture information is as current as necessary for accurate data.

Under certain industrial applications involving complex mixtures of related compounds (such as naturally occurring petroleum hydrocarbons), the removal of a specific component may not be achievable or necessarily desirable. For example, it is desirable to determine the amount of water vapor and free hydrocarbons that would be expected to condense out of well head vents from steam-injected wells at the anticipated operating temperature of a proposed collection condenser. This is a particularly difficult determination to make because the calculations (even if all the components and their molecular fraction were known) are very difficult to make and are not at all reliable. Additionally, once any collected sample drops below the anticipated condensation temperature, revaporization to create a representative mixture is not an easily accomplished task. However, with an instrument of this invention, a temperature controlled condenser would remove components that would in actuality be condensed at the condenser temperature. This condenser temperature can be varied over a range to achieve a dynamic condensation table useful at a number of temperatures. In no case does the instrument determine the amount of one component, just the total amount of material that condenses at a specific temperature and pressure.

As will be appreciated from the foregoing description, while it is presently preferred for the volume of each of the two pump heads, such as heads 18 and 19, to be equal in size and in volumetric pumping rate, this relationship is not required for the apparatus and method of this invention. Thus, the present invention can be utilized to determine amount of gas in a gas stream under conditions where the respective heads are not equal in size. For example, one can use the present invention to determine the amount of carbon dioxide in a high moisture stream of about 50% water. Here, the first pump head can and preferably does have a volume which is 100% greater than the volume of the second pump head. In operation, water is removed and carbon dioxide is removed as taught herein. The remaining or residual gas is fed back into the second head. With this arrangement, a low range, high accuracy flow meter is employed for meter 33 and such monitors the carbon dioxide only.

While the foregoing description makes use of illustrative embodiments and examples of various types, no limitations upon the present invention are to be implied or inferred therefrom.

What is claimed is:

1. A method for identifying the amount of a component portion of a sample gas comprising the steps of:
   (a) first pumping said sample gas at a first predetermined volumetric flow rate into a processing zone;
   (b) removing in said processing zone a component portion from said sample gas;
   (c) admixing a make-up gas with the remaining sample gas to produce a gas mixture while concurrently
      (1) secondly pumping said gas mixture at a second predetermined volumetric flow rate that is constant relative to said first predetermined volumetric flow rate, and
      (2) measuring the flow rate at which said make-up gas is so admixed; and
   (d) comparing said so measured make-up gas flow rate with said first predetermined volumetric flow rate.

2. The method of claim 1 wherein said first predetermined volumetric flow rate is substantially equal to said second predetermined volumetric flow rate.

3. The method of claim 1 wherein said first pumping and said second pumping are each carried out in respective first and second pump heads of a dual headed peristaltic pump, wherein said first and said second pump heads rotate on a common shaft and wherein said first and said second pump heads each have the same volumetric capacity.

4. The method of claim 1 wherein, prior to and during each of said first pumping and said second pumping, said sample gas and said gas mixture are each heated to a predetermined temperature.

5. The method of claim 4 wherein said predetermined temperature is the same for each of said sample gas and said gas mixture.

6. The method of claim 5 wherein said predetermined temperature is in the range of about 93° to about 107° C.

7. The method of claim 5 wherein said measuring is carried out with a mass flow metering means.

8. The method of claim 5 wherein said measuring is carried out with a laminar flow metering means.

9. The method of claim 1 wherein said make-up gas comprises air, said air is dried before being so admixed and so measured.

10. The method of claim 1 wherein said sample gas comprises a mixture of at least two different component gases and wherein during said removing one component of said sample gas is so removed before said admixing.

11. The method of claim 1 wherein said sample gas comprises a mixture of at least three different component gases, and wherein during said removing, at least two components of said sample gas are removed therefrom.

12. The method of claim 1 wherein said sample gas comprises a mixture of at least two different component gases, and wherein, during said removing, said sample gas is subjected to condensation conditions carried out at a predetermined temperature so as to remove from said sample gas all components thereof which condense at said predetermined temperature.

13. The method of claim 1 wherein said sample gas comprises a mixture of at least two different component gases, and wherein (a) in said processing zone, a plurality of separate subzones are provided which are tubularly interconnected together in a predetermined array, and each said subzone is adapted to substantially completely remove from said sample gas a different one predetermined respective component thereof when said sample gas, or a residual portion thereof, passes therethrough; and (b) said processing zone is provided with valve means so that said sample gas and/or residual portions thereof can be channeled for passage through said array along a predetermined pathway.

14. The method of claim 1 wherein said sample gas contains water vapor and at least one other gaseous component gas, and wherein said water vapor is removed from said sample gas during said removing.

15. The method of claim 1 wherein said sample gas contains carbon dioxide and at least one other gaseous component, and said carbon dioxide is removed from said sample gas during said removing.

16. The method of claim 1 wherein said sample gas contains gaseous carbon dioxide, water vapor, and at least one other gaseous component, and wherein both said water vapor and said carbon dioxide are so removed from said sample gas during said removing.

17. The method of claim 1 wherein, prior to said first pumping, said first predetermined volumetric flow rate and said second predetermined volumetric flow rate are each calibrated at a predetermined temperature and said first pumping and said second pumping are each carried out at said predetermined temperature.

18. The method of claim 1 which is computer controlled.

19. A method for monitoring the amount of moisture present in a continuously fed multi-component sample gas that contains moisture as one component thereof, said method comprising the steps of:
(a) heating said sample gas to a predetermined temperature;
(b) first pumping said so heated sample gas at a first predetermined constant volumetric flow rate through one pump head of a dual headed peristaltic pump means into a drying zone while maintaining said predetermined temperature;
(c) removing in the drying zone all moisture from said sample gas to produce a residual gas;
(d) admixing a continuously fed make-up gas with said residual gas while measuring the flow rate of said make-up gas so admixed so as to produce a resulting gas mixture;
(e) heating said resulting gas mixture to said predetermined temperature; and
(f) second pumping said so heated resulting gas mixture at a second predetermined constant volumetric flow rate through said second pump head of said dual headed peristaltic pump means, said second predetermined constant volumetric flow rate being substantially equal to said first predetermined constant volumetric flow rate; so that said so measured flow rate of said make-up gas is equal to said volume of said so removed moisture.

20. The method of claim 19 wherein said predetermined temperature is in the range of about 93° to about 107° C.

21. The method of claim 19 wherein said make-up gas comprises dry air and wherein said measuring is carried out with a mass flow meter.

22. The method of claim 19 wherein said removing is carried out in a drying zone, and wherein, in said drying zone, said sample gas is passed successively through a dehydrating membrane and a bed of anhydrous calcium sulfate having a highly porous granular structure and a high affinity for water.

23. The method of claim 22 wherein said resulting gas mixture is cycled through a jacket located about said drying zone after said second pumping.

24. The method of claim 19 wherein any variation in respective volumes of said first and said second pump heads is determined by a preliminary calibration procedure, and said calibration procedure comprises replacing said so fed sample gas with said so fed make-up gas, and allowing said make-up gas to flow through both of said pump heads while measuring the amount of said make-up gas flowing into each of said first pump head and said second pump head so that the difference in flow rates through each of said first and said second pump heads is measurable at said predetermined temperature.

25. The method of claim 24 wherein flow pulses created by the peristaltic pump heads are dampened.

26. An apparatus for monitoring the amount of at least one component present in a multi-component sample gas comprising in combination:
(a) means for removing at least one predetermined component from a multi-component sample gas to produce a resulting gas;
(b) first pump means including associated heat exchange means for pumping the sample gas at a first predetermined constant volumetric flow rate into and through said removing means;
(c) admixing means for adding a make-up gas to said resulting gas issuing from said removing means to produce a gas mixture;
(d) measuring means for determining the amount of said make-up gas so added at said admixing means;
(e) second pump means including associated heat exchange means for pumping said gas mixture at a second constant predetermined volumetric flow rate which is constant relative to said first constant volumetric flow rate;
(f) tube means interconnecting said first pump means, said removing means, said admixing means and said second pump means; and
(g) temperature regulation means for maintaining said first pump means and said second pump means, at a predetermined temperature;
so that the flow rate of said make-up gas as determined by said measuring means is representative of the amount of said predetermined component present in said sample gas.

27. The apparatus of claim 26 wherein said first pump means and said second pump means are respective first and second heads of a constant volume peristaltic pump means.

28. The apparatus of claim 26 wherein said first and second heads are substantially identical and operate on a common drive shaft.

29. The apparatus of claim 26 wherein said admixing means comprises air drying means, and connector means associating said air drying means with tube means conveying said resulting gas.

30. The apparatus of claim 29 which further includes calibration means, and said calibration means includes tube and associated valve means for feeding dry air from said air drying means through said apparatus in place of sample gas.

31. The apparatus of claim 26 wherein said measuring means comprises a mass flow meter.

32. The apparatus of claim 26 wherein said measuring means comprises a laminar flow sensing means.

33. The apparatus of claim 26 wherein said temperature regulation means comprises in combination:
  (a) box means enclosing said first pump means, said admixing means said measuring means, said second pump means, and associated portions of said tube means;
  (b) first coil means within said box means through which said sample gas is circulated before entering said first pump means, including connecting tube means;
  (c) second coil means within said box means through which said gas mixture is circulated before entering said second pump means, including connection tube means;
  (d) electric heating means for heating said box means; and
  (e) temperature regulation means for said heating means.

34. The apparatus of claim 26 which includes means for operation of said apparatus in a calibration mode.

35. The apparatus of claim 26 wherein said means for removing comprises water vapor removal means.

36. The apparatus of claim 26 wherein said means for removing comprises carbon dioxide removal means.

37. The apparatus of claim 26 wherein said means for removing comprises both water vapor removal means and carbon dioxide removal means.

38. The apparatus of claim 26 wherein said means for removing selectively removes one component from said sample gas.

39. The apparatus of claim 26 wherein said means for removing selectively removes at least two components from said sample gas.

40. The apparatus of claim 39 wherein said means for removing comprises a plurality of gas component removal means, tube means interconnecting said removal means together, and valve means for selective operation of at least one of said removal means without selected others thereof.

41. The apparatus of claim 26 which further includes computer control means for operating same.

* * * * *